(12) United States Patent
Yang et al.

(10) Patent No.: US 11,700,768 B2
(45) Date of Patent: Jul. 11, 2023

(54) COMPOUND AND ORGANIC LIGHT EMITTING DEVICE COMPRISING THE SAME

(71) Applicant: LG CHEM, LTD., Seoul (KR)

(72) Inventors: Jung Hoon Yang, Daejeon (KR); Dong Hoon Lee, Daejeon (KR); Jung Oh Huh, Daejeon (KR); Boon Jae Jang, Daejeon (KR); Min Young Kang, Daejeon (KR); Dong Uk Heo, Daejeon (KR); Mi Yeon Han, Daejeon (KR); Min Woo Jung, Daejeon (KR)

(73) Assignee: LG CHEM, LTD., Seoul (KR)

( * ) Notice: Subject to any disclaimer, the term of this patent is extended or adjusted under 35 U.S.C. 154(b) by 407 days.

(21) Appl. No.: 16/475,239

(22) PCT Filed: Mar. 13, 2018

(86) PCT No.: PCT/KR2018/002940
§ 371 (c)(1),
(2) Date: Jul. 1, 2019

(87) PCT Pub. No.: WO2018/199466
PCT Pub. Date: Nov. 1, 2018

(65) Prior Publication Data
US 2019/0341558 A1    Nov. 7, 2019

(30) Foreign Application Priority Data

Apr. 27, 2017 (KR) .................. 10-2017-0054611
Mar. 6, 2018 (KR) .................. 10-2018-0026391

(51) Int. Cl.
*H10K 85/60* (2023.01)
*C07D 471/04* (2006.01)
(Continued)

(52) U.S. Cl.
CPC ....... *H10K 85/6572* (2023.02); *C07D 471/04* (2013.01); *C07F 9/6561* (2013.01);
(Continued)

(58) Field of Classification Search
CPC .. C07D 519/00; C07D 471/04; C07D 307/91; C07D 333/76; C07D 487/04;
(Continued)

(56) References Cited

U.S. PATENT DOCUMENTS 7,989,644 B2    8/2011  Tanabe et al.
10,937,984 B2 *  3/2021  Shin .................... H01L 27/3209
(Continued)

FOREIGN PATENT DOCUMENTS

CN    101184822 A    5/2008
CN    105321984 A    2/2016
(Continued)

OTHER PUBLICATIONS

Machine translation for CN 106565705 A (publication date: Apr. 2017). (Year: 2017).*
(Continued)

*Primary Examiner* — Dawn L Garrett
(74) *Attorney, Agent, or Firm* — Dentons US LLP

(57) ABSTRACT

Provided is a compound of Formula 1:

[Formula 1]

(Continued)

where X is O or S; $Ar_1$ is an aryl having 6 to 20 carbon atoms substituted with at least one functional group selected from the group consisting of cyano, pyridinyl, benzimidazolyl and diphenylphosphine oxide, or a substituted or unsubstituted heteroaryl having 3 to 20 carbon atoms containing at least one N; and $Ar_2$ is a functional group of Formula 2 below, with the proviso that $Ar_1$ and $Ar_2$ are different from each other,

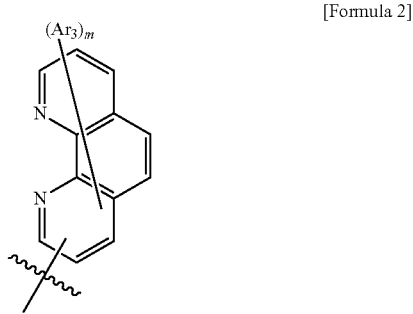

[Formula 2]

where $Ar_3$ is an aryl having 6 to 20 carbon atoms, and m is an integer of 0 to 2, and an organic light emitting device comprising the same.

6 Claims, 1 Drawing Sheet

(51) Int. Cl.
    *C07F 9/6561*     (2006.01)
    *C09K 11/06*     (2006.01)
    *H10K 50/16*     (2023.01)
    *H10K 50/17*     (2023.01)

(52) U.S. Cl.
    CPC ............ *C09K 11/06* (2013.01); *H10K 85/615* (2023.02); *H10K 85/654* (2023.02); *H10K 85/6574* (2023.02); *H10K 85/6576* (2023.02); *C09K 2211/1018* (2013.01); *H10K 50/16* (2023.02); *H10K 50/171* (2023.02)

(58) Field of Classification Search
    CPC .................. C07F 9/6561; C09K 11/06; C09K 2211/1018; H01L 51/00; H01L 51/0052; H01L 51/0067; H01L 51/0072; H01L 51/0073; H01L 51/0074; H01L 51/50; H01L 51/5072; H01L 51/5092; H10K 85/6572; H10K 85/615; H10K 85/654; H10K 85/6574; H10K 85/6576; H10K 50/16; H10K 50/171; H10K 50/00; H10K 99/00; H10K 50/11
See application file for complete search history.

(56) References Cited

U.S. PATENT DOCUMENTS

| | | | |
|---|---|---|---|
| 2004/0076853 A1* | 4/2004 | Jarikov | H01L 51/5012 428/690 |
| 2004/0251816 A1 | 12/2004 | Leo et al. | |
| 2009/0131673 A1* | 5/2009 | Tanabe | C07D 409/14 546/88 |
| 2014/0077191 A1 | 3/2014 | Mizutani et al. | |
| 2015/0131302 A1 | 5/2015 | Inoue et al. | |
| 2016/0043327 A1 | 2/2016 | Yoo et al. | |
| 2016/0181548 A1 | 6/2016 | Parham et al. | |
| 2016/0268516 A1 | 9/2016 | Tanaka et al. | |
| 2017/0186965 A1 | 6/2017 | Parham et al. | |
| 2018/0269402 A1 | 9/2018 | Huh et al. | |
| 2019/0165282 A1* | 5/2019 | Parham | C07D 409/14 |

FOREIGN PATENT DOCUMENTS

| | | |
|---|---|---|
| CN | 106459018 A | 2/2017 |
| CN | 106565705 | 4/2017 |
| EP | 2983227 A1 | 2/2016 |
| JP | 2013-100239 | 5/2013 |
| JP | 2014-103103 | 6/2014 |
| KR | 10-2013-0080872 | 7/2013 |
| KR | 10-2015-0054797 | 5/2015 |
| KR | 10-2015-0055553 | 5/2015 |
| KR | 10-2015-0074603 | 7/2015 |
| KR | 10-1560102 | 10/2015 |
| KR | 10-2015-0136027 | 12/2015 |
| KR | 10-2016-0018332 | 2/2016 |
| KR | 10-2016-0028524 | 3/2016 |
| KR | 10-2017-0113469 | 10/2017 |
| WO | 2003012890 | 2/2003 |
| WO | 2013157495 | 10/2013 |
| WO | 2015014434 | 2/2015 |
| WO | 2015022987 | 2/2015 |
| WO | 2016-097983 | 6/2016 |
| WO | 2016108596 | 7/2016 |
| WO | 2016143508 | 9/2016 |
| WO | 2016175023 | 11/2016 |

OTHER PUBLICATIONS

J. Materials Chemistry C, (2017), vol. 5, pp. 2329-2336. (Year: 2017).*
Han et al., Chemistry—A European Journal 19, No. 4 (2013): 1385-1396. (Year: 2013).*
Han et al., "Short-axis substitution approach selectively optimizes electrical properties of dibenzothiophene-based phosphine oxide hosts." Journal of the American Chemical Society 134, No. 46 (2012): 19179-19188. (Year: 2012).*
International Search Report and the Written Opinion of PCT/KR2018/002940, dated Jul. 6, 2018
Office Action of Chinese Patent Office in Appl'n No. 201880006666.4, dated Sep. 27, 2022.

* cited by examiner

【FIG. 1】
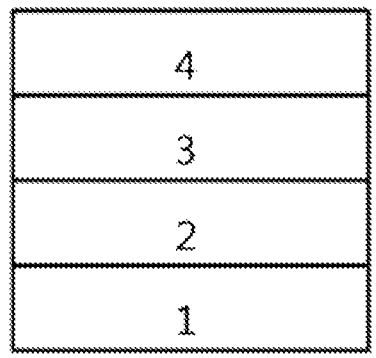
【FIG. 2】
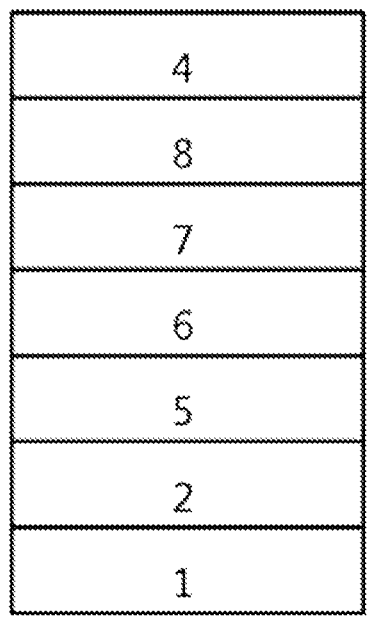

COMPOUND AND ORGANIC LIGHT EMITTING DEVICE COMPRISING THE SAME

CROSS-REFERENCE TO RELATED APPLICATIONS

This application is a National Stage Application of International Application No. PCT/KR2018/002940 filed on Mar. 13, 2018, which claims the benefit of priority from Korean Patent Application No. 10-2017-0054611 filed on Apr. 27, 2017 and Korean Patent Application No. 10-2018-0026391 filed on Mar. 6, 2018, the full disclosures of which are incorporated herein by reference.

TECHNICAL FIELD

The present invention relates to a novel compound and an organic light emitting device comprising the same.

BACKGROUND ART

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently has a multilayered structure that comprises different materials in order to enhance efficiency and stability of the organic light emitting device, and for example, the organic material layer can be formed of a hole injection layer, a hole transport layer, a light emitting layer, an electron transport layer, an electron injection layer and the like. In the structure of the organic light emitting device, if a voltage is applied between two electrodes, the holes are injected from an anode into the organic material layer and the electrons are injected from the cathode into the organic material layer, and when the injected holes and the electrons meet each other, an exciton is formed, and light is emitted when the exciton falls to a ground state again.

There is a continuing need for the development of new materials for the organic materials used in such organic light emitting devices.

DETAILED DESCRIPTION OF THE INVENTION

Technical Problem

The present invention relates to a novel compound and an organic light emitting device comprising the same.

Technical Solution

The present invention provides a compound of Formula 1:

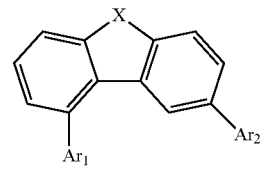

[Formula 1]

wherein in Formula 1:
X is an oxygen atom (O) or a sulfur atom (S);
$Ar_1$ is selected from the group consisting of an aryl having 6 to 20 carbon atoms substituted with at least one functional group selected from the group consisting of cyano, pyridinyl, benzimidazolyl and diphenylphosphine oxide, and a substituted or unsubstituted heteroaryl having 3 to 20 carbon atoms containing at least one N;
$Ar_2$ is a functional group of Formula 2 below, with the proviso that $Ar_1$ and $Ar_2$ are different from each other:

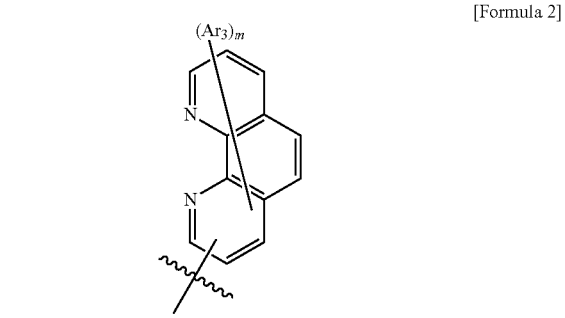

[Formula 2]

in Formula 2:
$Ar_3$ is an aryl having 6 to 20 carbon atoms; and
m is an integer of 0 to 2.

The present invention also provides an organic light emitting device comprising a first electrode; a second electrode provided at a side opposite to the first electrode; and at least one layer of an organic material layer provided between the first electrode and the second electrode, wherein the at least one layer of the organic material layer includes a compound of Formula 1.

Advantageous Effects

The compound of Formula 1 described above can be used as a material of the organic material layer of the organic light emitting device, and enables improvement of the efficiency, low driving voltage and/or improvement of the lifetime characteristic when applied to the organic light emitting device. Particularly, the compound of Formula 1 can be used as a light emitting, electron transport or electron injecting material.

BRIEF DESCRIPTION OF DRAWINGS

FIG. 1 shows an example of an organic light emitting device comprising a substrate 1, an anode 2, a light emitting layer 3, and a cathode 4.

FIG. 2 shows an example of an organic light emitting device comprising a substrate 1, an anode 2, a hole injection layer 5, a hole transport layer 6, a light emitting layer 7, an electron transport layer 8, and a cathode 4.

DETAILED DESCRIPTION OF THE EMBODIMENTS

Hereinafter, the present invention will be described in more detail to help understanding of the present invention.

In the present specification,

means a bond connected to another substituent group.

As used herein, the term "substituted or unsubstituted" means that substitution is performed by one or more substituent groups selected from the group consisting of deuterium, a halogen group, a nitrile group, a nitro group, a hydroxyl group, a carbonyl group, an ester group, an imide group, an amino group, a phosphine oxide group, an alkoxy group, an aryloxy group, an alkylthioxy group, an arylthioxy group, an alkylsulfoxy group, are arylsulfoxy group, a silyl group, a boron group, an alkyl group, a cycloalkyl group, air alkenyl group, an aryl group, an aralkyl group, an aralkenyl group, an alkylaryl group, an alkylamine group, an aralkylamine group, a heteroarylamine group, an arylamine group, an arylphosphine group, and a heterocyclic group containing at least one of N, O, and S atoms, or there is no substituent group, or substitution is performed by a substituent group where two or more substituent groups of the exemplified substituent groups are linked or there is no substituent group. For example, the term "substituent group where two or more substituent groups are linked" can be a biphenyl group. That is, the biphenyl group can be an aryl group, or can be interpreted as a substituent group where two phenyl groups are connected.

In the present specification, the number of carbon atoms in a carbonyl group is not particularly limited, but is preferably 1 to 40. Specifically, the carbonyl group can be compounds having the following structures, but is not limited thereto.

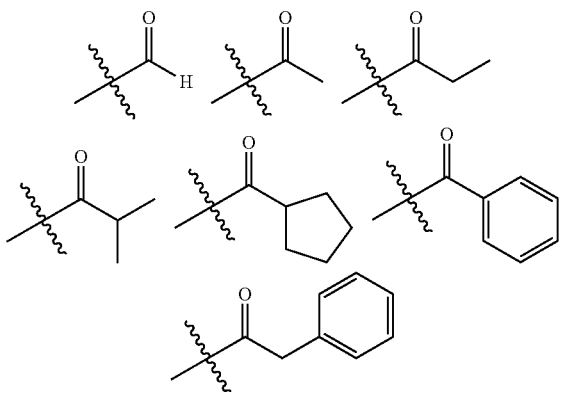

In the present specification, the ester group can have a structure in which hydrogen of the carboxyl group can be substituted by a straight-chain, branched-chain, or cyclic alkyl group having 1 to 25 carbon atoms, or an aryl group having 6 to 25 carbon atoms. Specifically, the ester group can be compounds having the following structures, but is not limited thereto.

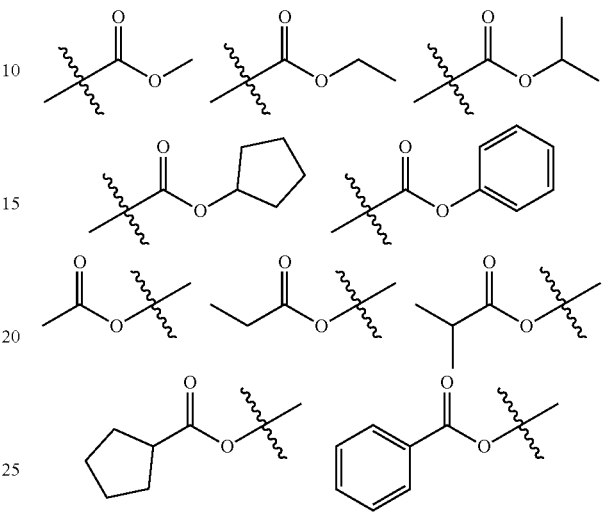

In the present specification, the number of carbon atoms in an imide group is not particularly limited, but is preferably 1 to 25. Specifically, the imide group can be compounds having the following structures, but is not limited thereto.

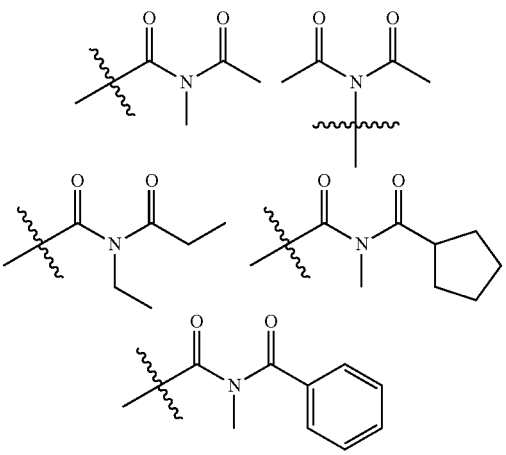

In the present specification, the silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but is not limited thereto.

In the present specification, the boron group specifically includes a trimethylboron group, a triethylboron group, a t-butyldimethylboron group, a triphenylboron group, a phenylboron group, and the like, but is not limited thereto.

In the present specification, examples of a halogen group include fluorine, chlorine, bromine, and iodine.

In the present specification, the alkyl group can be a straight chain or a branched chain, and the number of carbon atoms thereof is not particularly limited, but is preferably 1 to 40. According to one embodiment, the alkyl group has 1 to 20 carbon atoms. According to another embodiment, the alkyl group has 1 to 10 carbon atoms. According to still another embodiment, the alkyl group has 1 to 6 carbon atoms. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethyl-butyl, heptyl, n-heptyl, 1-methylhexyl, cyclopentyl-methyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methyl-hexyl, and the like, but are not limited thereto.

In the present specification, the alkenyl group can be a straight chain or a branched chain, and the number of carbon atoms thereof is not particularly limited, but is preferably 2 to 40. According to one embodiment, the alkenyl group has 2 to 20 carbon atoms. According to another embodiment, the alkenyl group has 2 to 10 carbon atoms. According to still another embodiment, the alkenyl group has 2 to 6 carbon atoms. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenyl-vinyl-1-yl, 2,2-diphenyl-vinyl-1-yl, 2-phenyl-2-(naphthyl-1-yl)vinyl-1-yl, 2,2-bis(di-phenyl-1-yl)-vinyl-1-yl, a stilbenyl group, a styrenyl group, and the like, but are not limited thereto.

In the present specification, the cycloalkyl group is not particularly limited, but the number of carbon atoms thereof is preferably 3 to 60. According to one embodiment, the cycloalkyl group has 3 to 30 carbon atoms. According to another embodiment, the cycloalkyl group has 3 to 20 carbon atoms. According to another embodiment, the cycloalkyl group has 3 to 6 carbon atoms. Specific examples thereof include cyclopropyl, cyclobutyl, cyclopentyl, 3-methylcyclo-pentyl, 2,3-dimethylcyclopentyl, cyclohexyl, 3-methylcyclohexyl, 4-methylcyclohexyl, 2,3-dimethylcy-clohexyl, 3,4,5-trimethylcyclohexyl, 4-tert-butylcyclohexyl, cycloheptyl, cyclooctyl, and the like, but are not limited thereto.

In the present specification, the aryl group is not particularly limited, but preferably has 6 to 60 carbon atoms, and can be a monocyclic aryl group or a polycyclic aryl group. According to one embodiment, the aryl group has 6 to 30 carbon atoms. According to one embodiment, the aryl group has 6 to 20 carbon atoms. The aryl group can be a phenyl group, a biphenyl group, a terphenyl group or the like as the monocyclic aryl group, but is not limited thereto. Examples of the polycyclic aryl group include a naphthyl group, an anthracenyl group, a phenanthryl group, a pyrenyl group, a perylenyl group, a chrysenyl group, a fluorenyl group or the like, but is not limited thereto.

In the present specification, a fluorenyl group can be substituted, and two substituent groups can be linked with each other to form a spiro structure. In the case where the fluorenyl group is substituted,

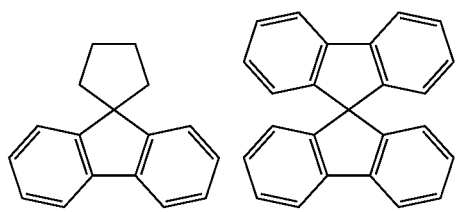

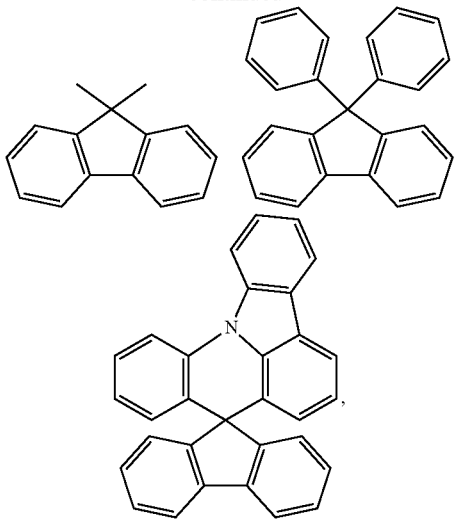

and the like can be formed. However, the structure is not limited thereto.

In the present specification, the heterocyclic group is a heterocyclic group containing at least one of O, N, Si and S as a heteroatom, and the number of carbon atoms thereof is not particularly limited, but is preferably 2 to 60. Examples of the heterocyclic group include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidi-nyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothi-ophene group, a dibenzothiophene group, a benzofuranyl group, a phenanthroline group, an isoxazolyl group, a thia-diazolyl group, a phenothiazinyl group, a dibenzofuranyl group, and the like, but are not limited thereto.

In the present specification, the aryl group in the aralkyl group, the aralkenyl group, the alkylaryl group, and the arylamine group is the same as the aforementioned examples of the aryl group. In the present specification, the alkyl group in the aralkyl group, the alkylaryl group and the alkylamine group is the same as the aforementioned examples of the alkyl group. In the present specification, the heteroaryl in the heteroarylamine can be applied to the aforementioned description of the heterocyclic group. In the present specification, the alkenyl group in the aralkenyl group is the same as the aforementioned examples of the alkenyl group. In the present specification, the aforementioned description of the aryl group can be applied except that the arylene is a divalent group. In the present specification, the aforementioned description of the heterocyclic group can be applied except that the heteroarylene is a divalent group. In the present specification, the aforementioned description of the aryl group or cycloalkyl group can be applied except that the hydrocarbon ring is not a monovalent group but formed by combining two substituent groups. In the present specification, the aforementioned description of the heterocyclic group can be applied, except that the heterocycle is not a monovalent group but formed by combining two substituent groups.

Meanwhile, the present invention provides a compound of Formula 1 below:

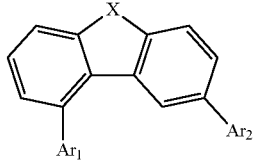

[Formula 1]

wherein in Formula 1:

X is O or S;

Ar$_1$ is selected from the group consisting of an aryl having 6 to 20 carbon atoms substituted with at least one functional group selected from the group consisting of cyano, pyridinyl, benzimidazolyl and diphenylphosphine oxide, and a substituted or unsubstituted heteroaryl group having 3 to 20 carbon atoms containing at least one N;

Ar$_2$ is a functional group of Formula 2 below, with the proviso that Ar$_1$ and Ar$_2$ are different from each other:

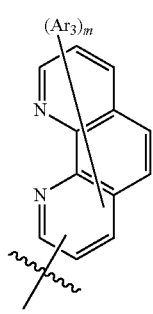

[Formula 2]

wherein in Formula 2:

Ar$_3$ is an aryl having 6 to 20 carbon atoms; and m is an integer of 0 to 2.

Specifically, in the Formula 1, the Ar$_1$ can be any one functional group selected from the group consisting of the following functional groups:

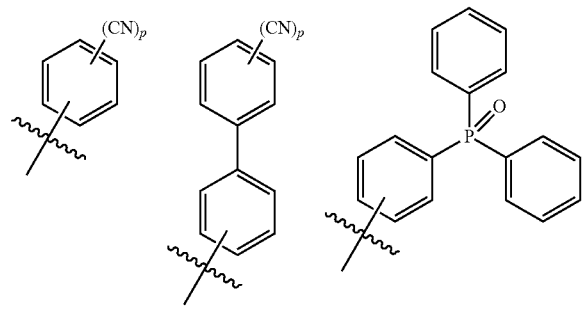

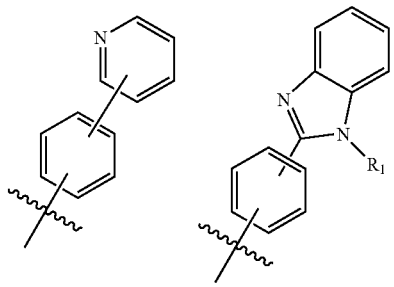

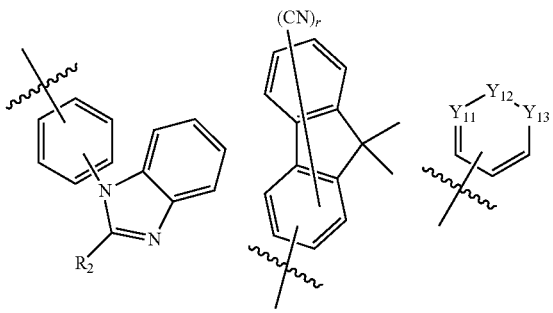

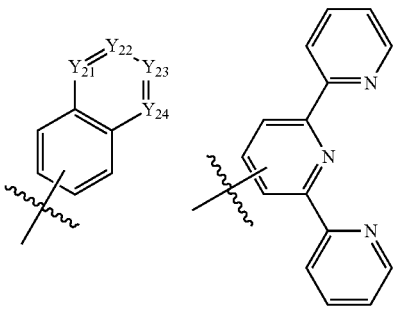

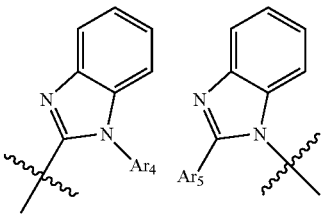

wherein:

Y$_{11}$, Y$_{12}$ and Y$_{13}$ are each independently —CH or N, with the proviso that at least one of Y$_{11}$, Y$_{12}$ and Y$_{13}$ is N;

Y$_{21}$, Y$_{22}$, Y$_{23}$ and Y$_{24}$ are each independently —CH or N, with the proviso that at least one of Y$_{21}$, Y$_{22}$, Y$_{23}$ and Y$_{24}$ is N;

Ar$_4$ and Ar$_5$ are each independently selected from the group consisting of hydrogen, deuterium, an alkyl having 1 to 20 carbon atoms, an aryl having 6 to 20 carbon atoms, and a heteroaryl having 3 to 20 carbon atoms containing at least one of N, Si and S;

R$_1$ and R$_2$ are each independently selected from the group consisting of hydrogen, deuterium, an alkyl having 1 to 20 carbon atoms, and an aryl having 6 to carbon atoms, and p, q and r are each independently an integer of 1 or 2.

More specifically, in the Formula 1, $Ar_1$ can be any one selected from the group consisting of the following functional groups:
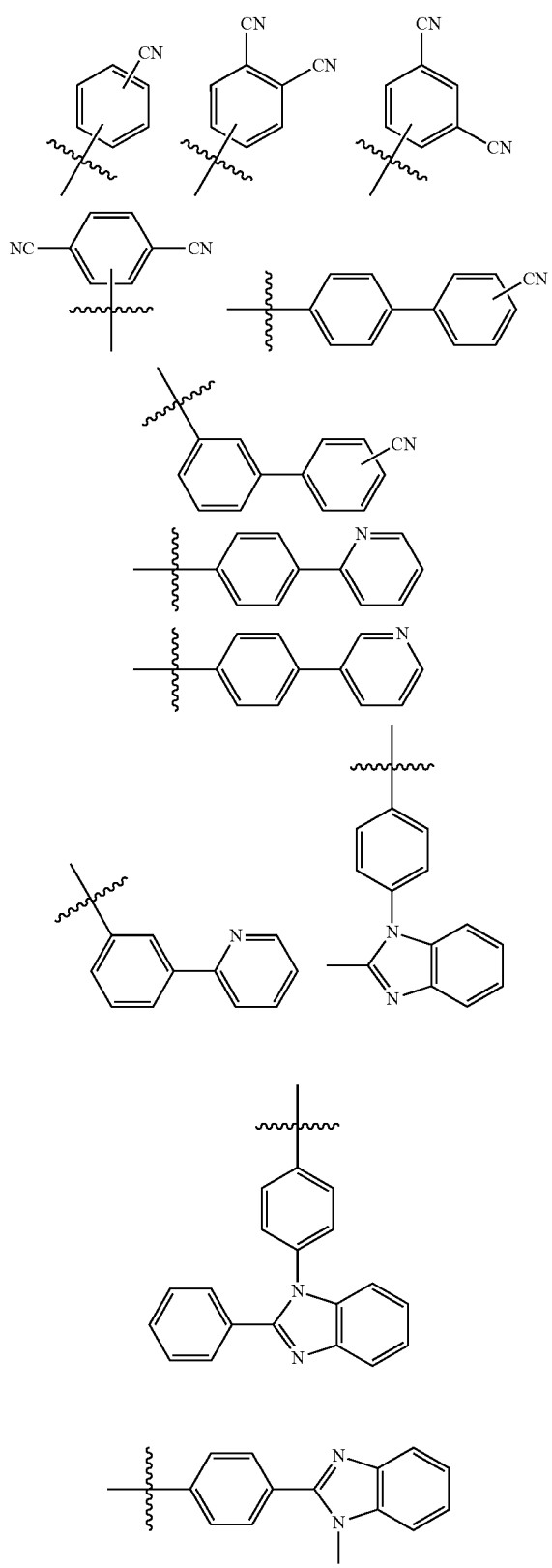
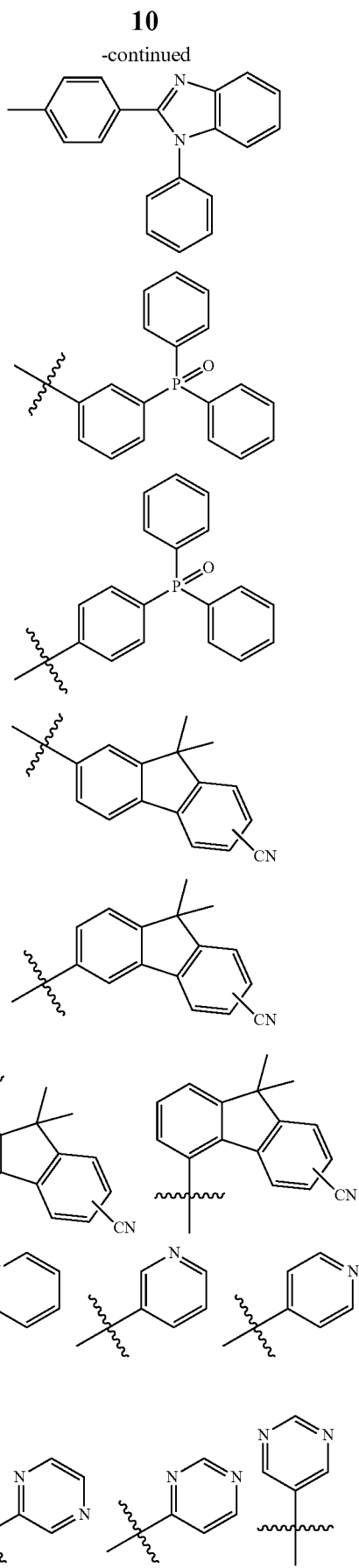

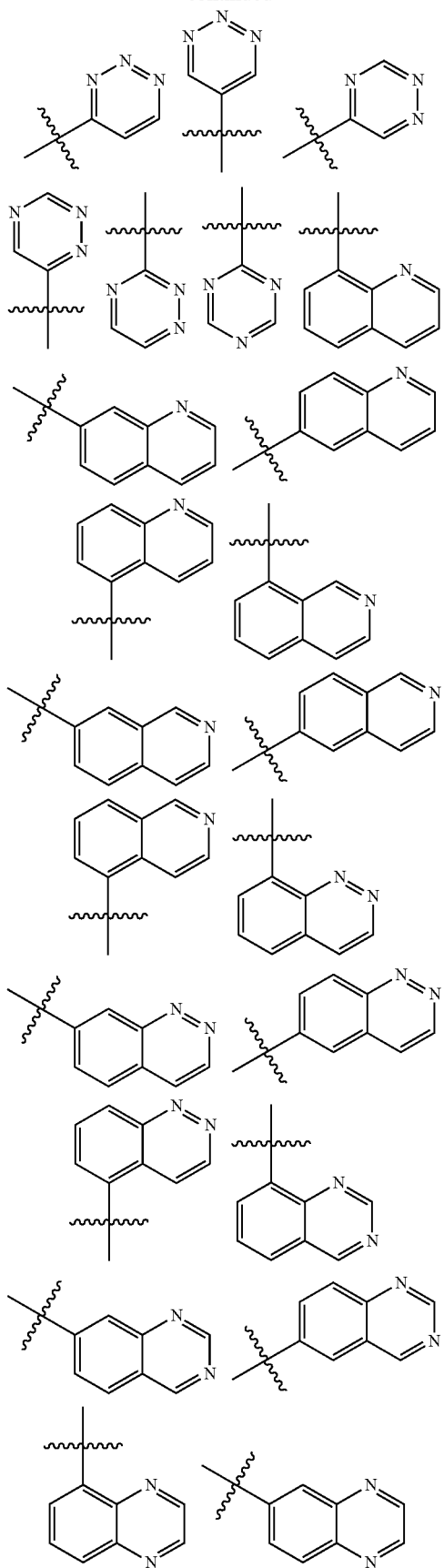
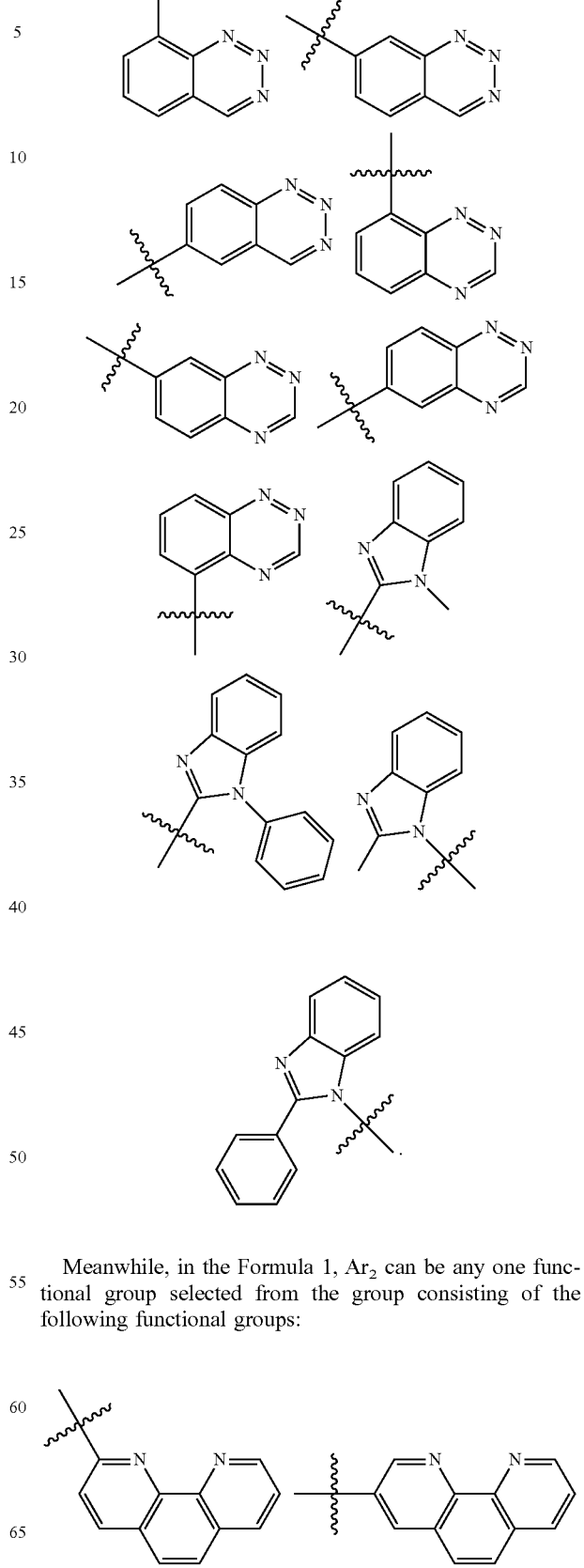
Meanwhile, in the Formula 1, $Ar_2$ can be any one functional group selected from the group consisting of the following functional groups:
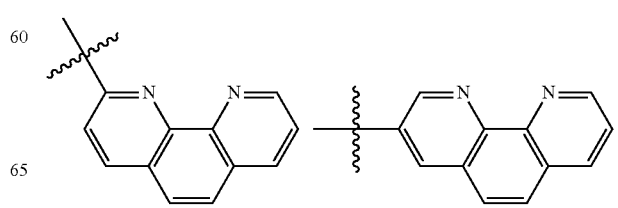

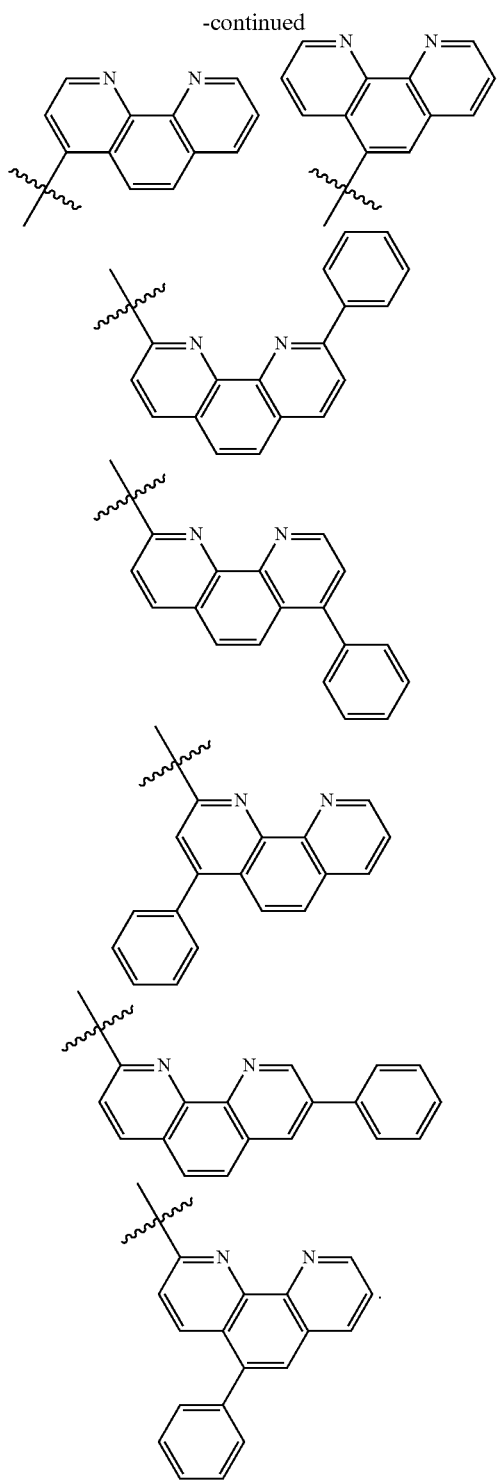

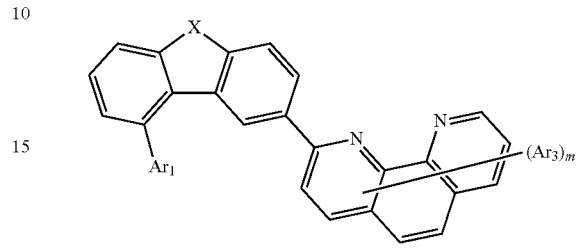

wherein in Formula 1a:

X is O or S:

Ar₁ is as defined above, with the proviso that Ar₁ is not [1,10]phenanthroline, and more specifically it can be selected from the group consisting of an aryl having 6 to 20 carbon atoms substituted with cyano, benzimidazolyl or diphenylphosphine oxide; a quinolinyl; and a terpyridinyl group, still more preferably, a phenyl substituted with a cyano group or a benzimidazole group, a fluorenyl substituted with a cyano group, or a quinolinyl;

Ar₃ is phenyl; and m is an integer of 0 or 1.

Representative examples of the compound of Formula 1 are as follows:

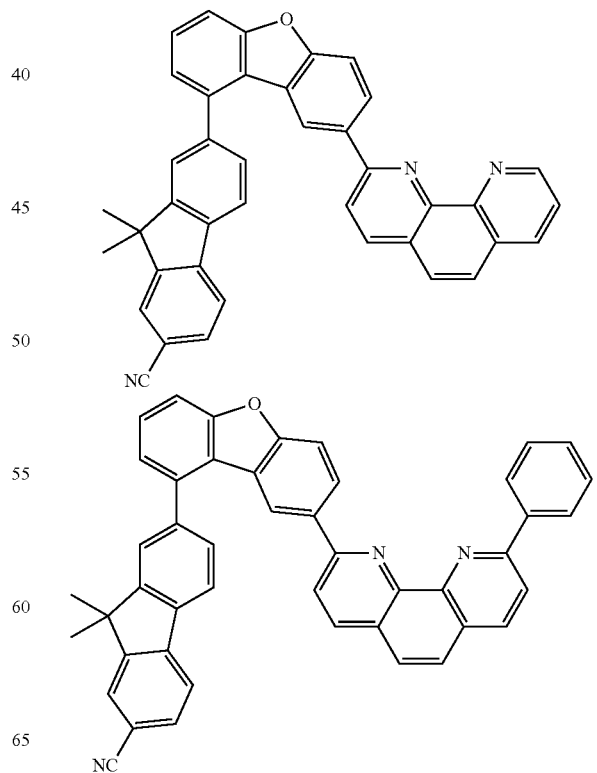

As the compound of Formula 1 has an asymmetrical structure in which functional groups Ar₂ and Ar₁ of the specific structure are respectively substituted at positions 5 and 9 with respect to the central structure of dibenzofuran or dibenzothiophene, the compound can have excellent thermal stability and less interaction between the substances, and better characteristics inherent to the material, compared to a compound having substituents symmetrically arranged on both sides of the central skeleton. As a result, when applied to an organic light emitting device, the present compound can exhibit superior characteristics in terms of driving voltage, efficiency and lifetime.

More specifically, considering the remarkable improvement of the effects by controlling the type of the functional groups Ar₁ and Ar₂ and the substitution position thereof, the compound of Formula 1 can be a compound of Formula 1a:

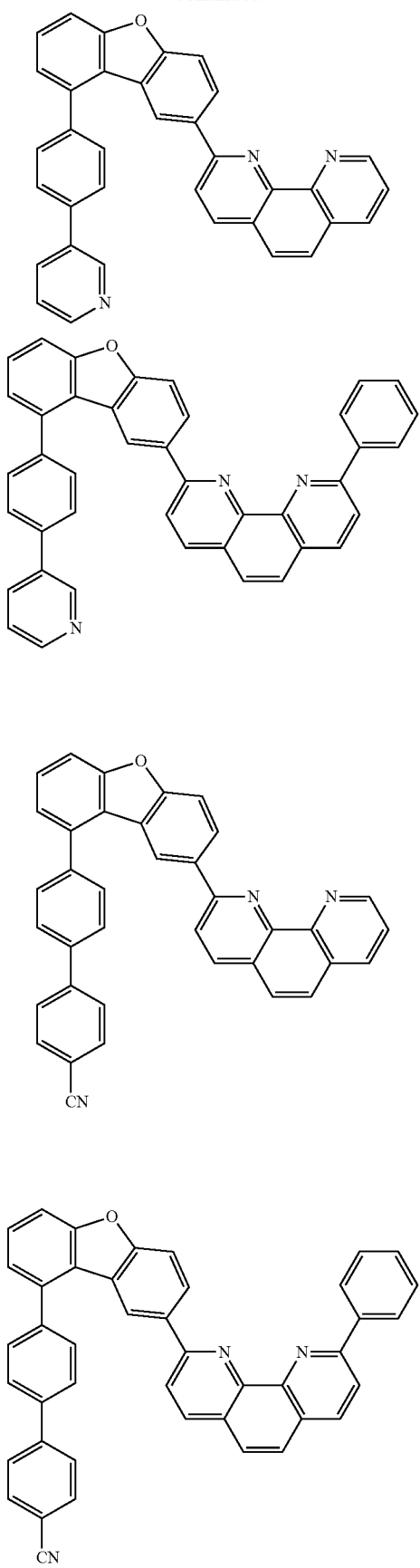

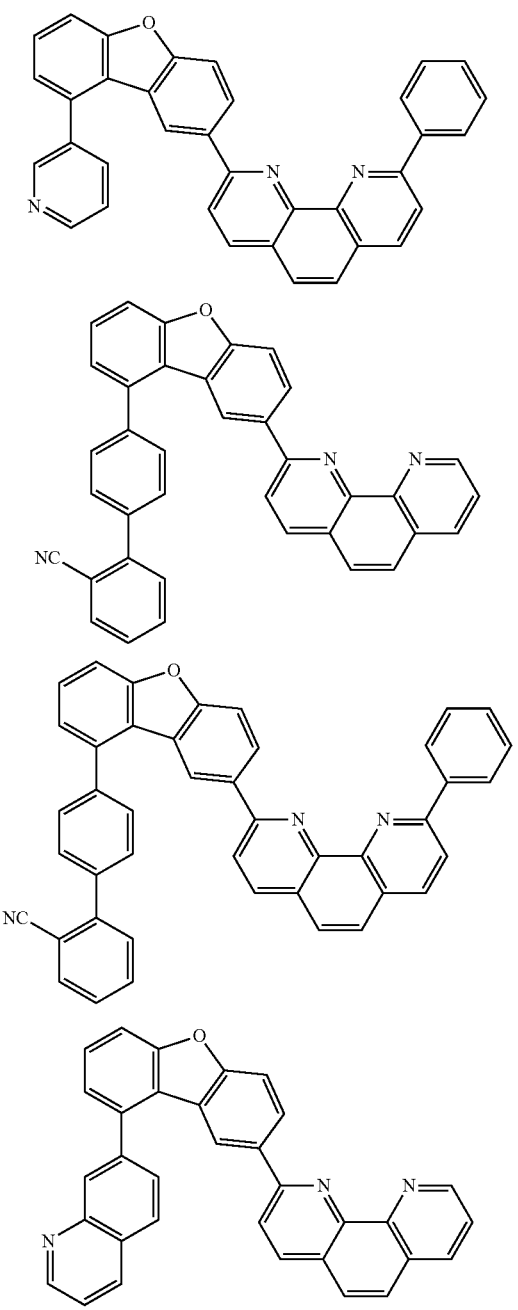
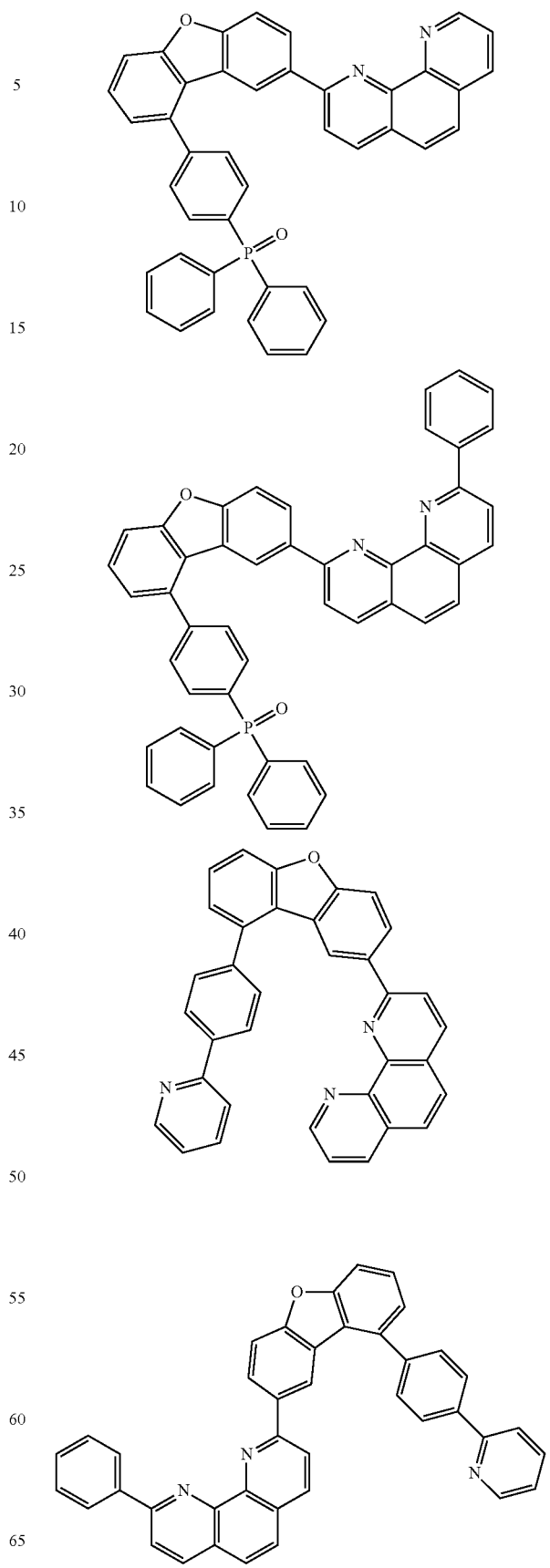

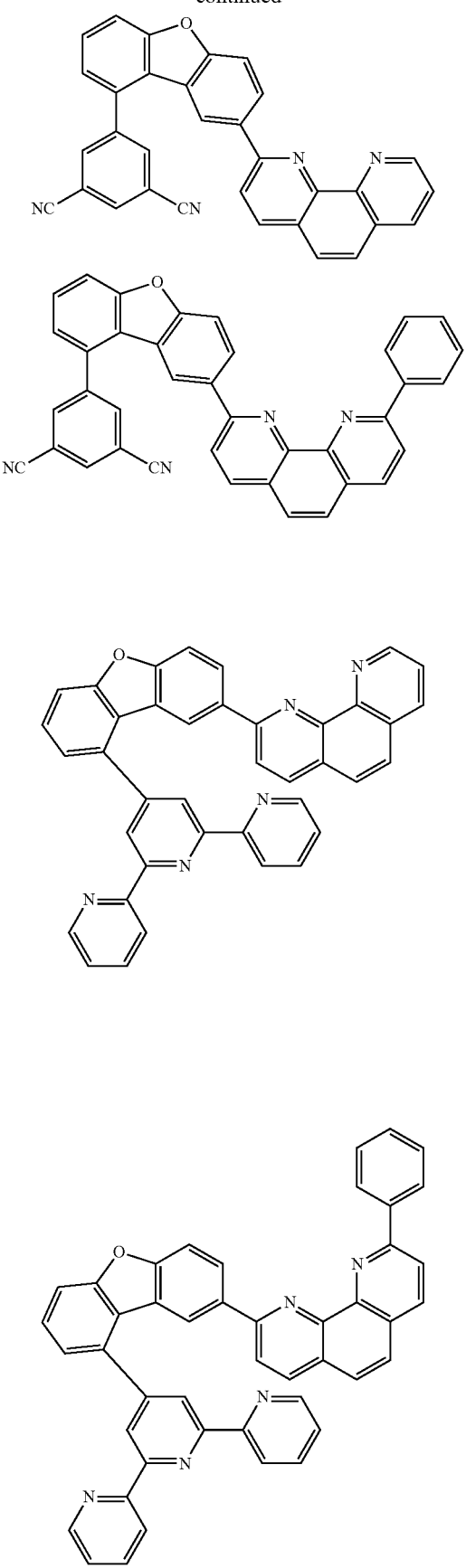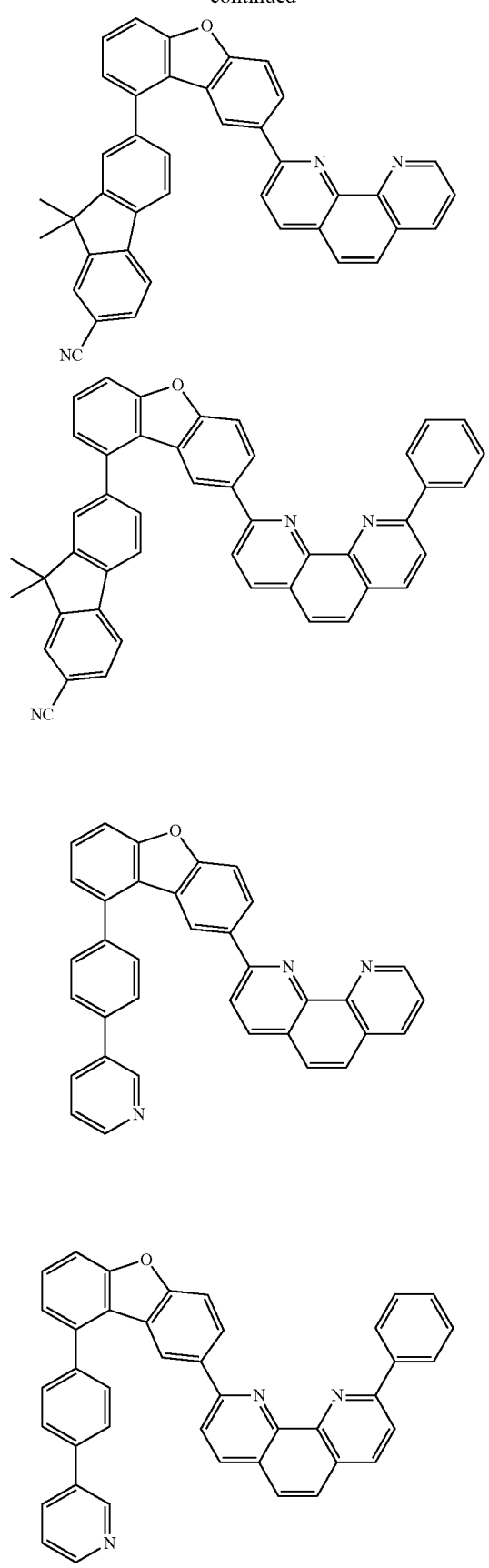

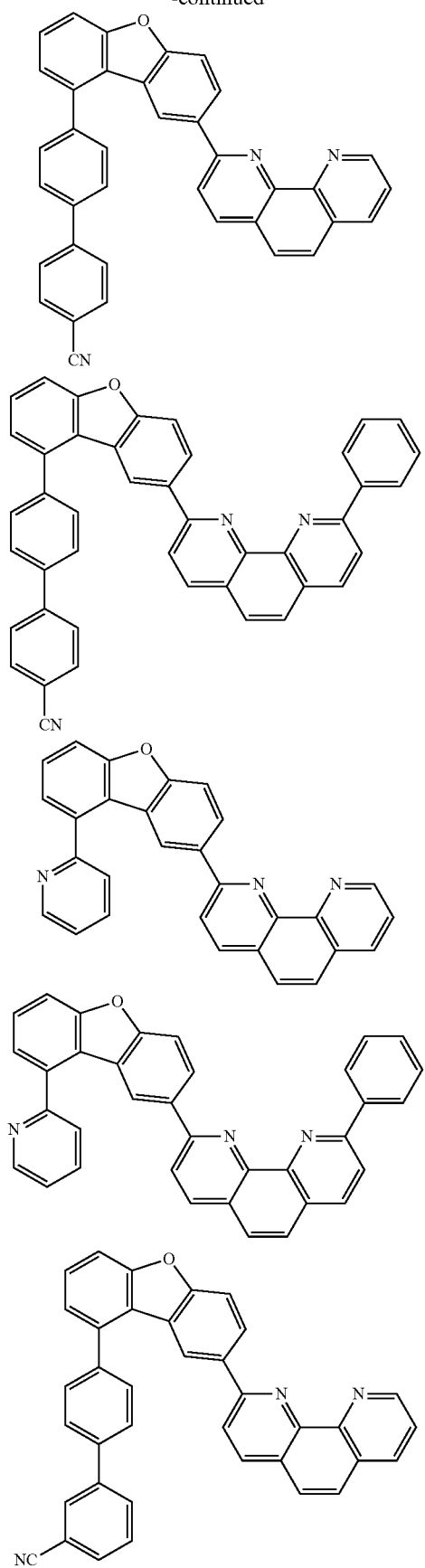
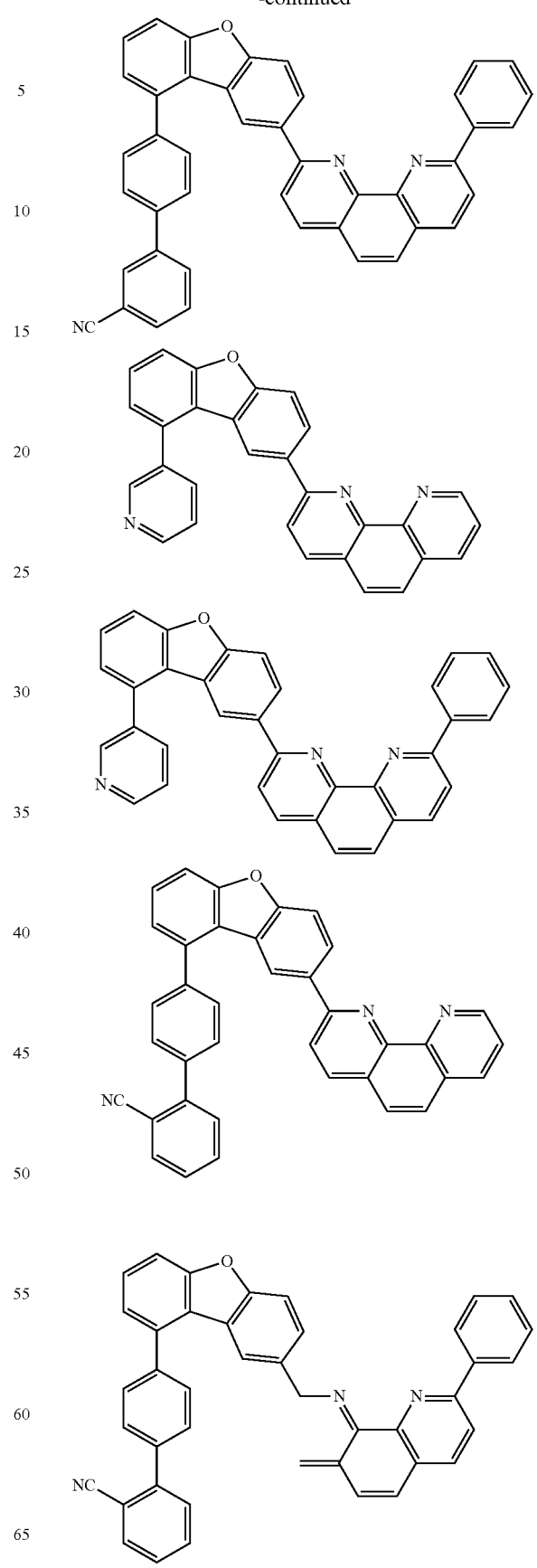

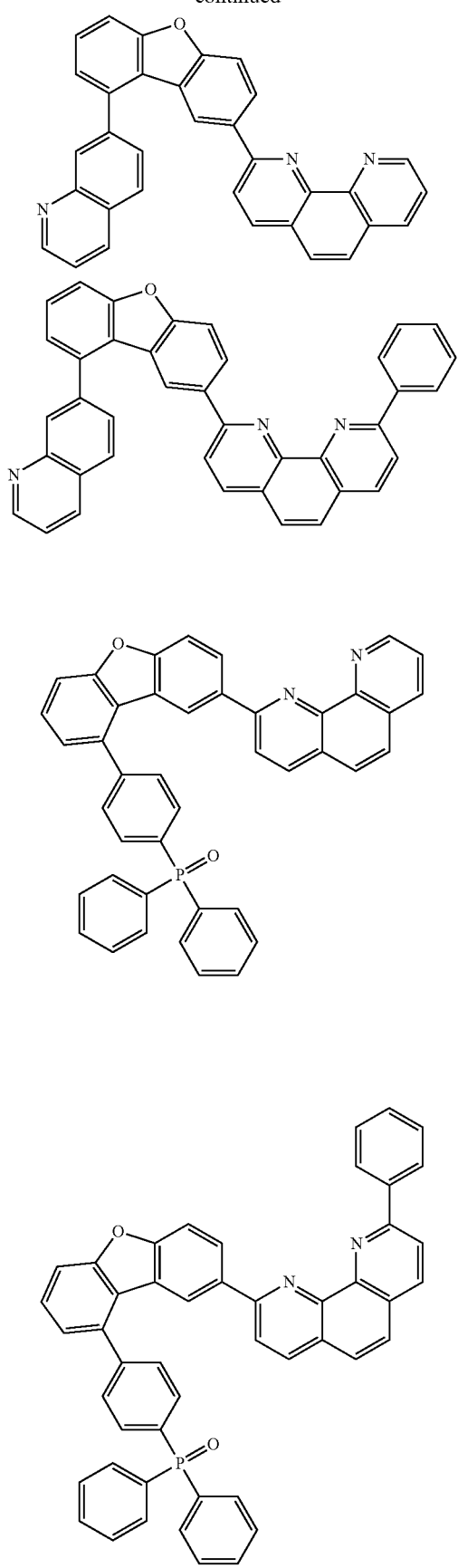

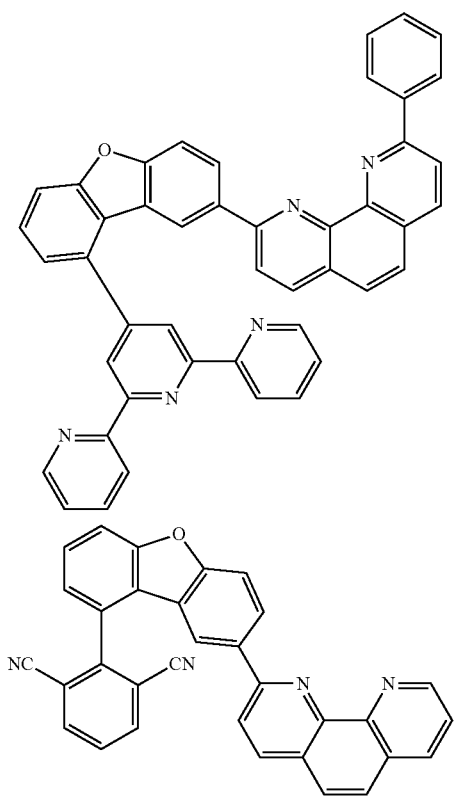
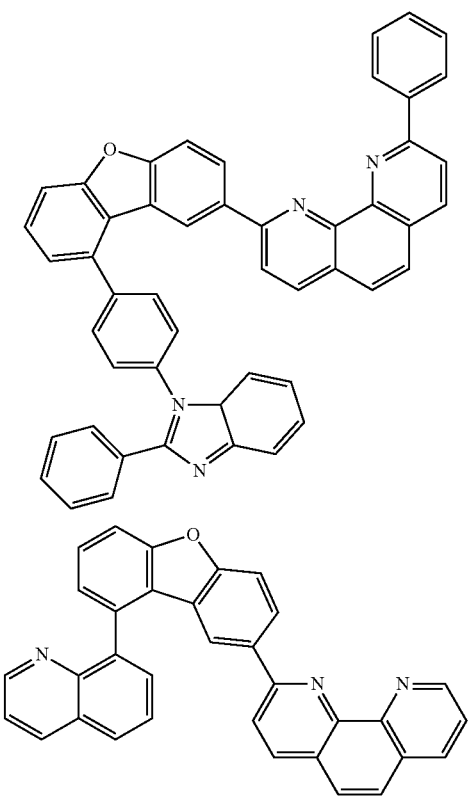
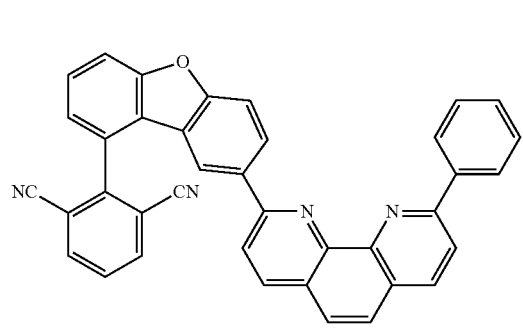
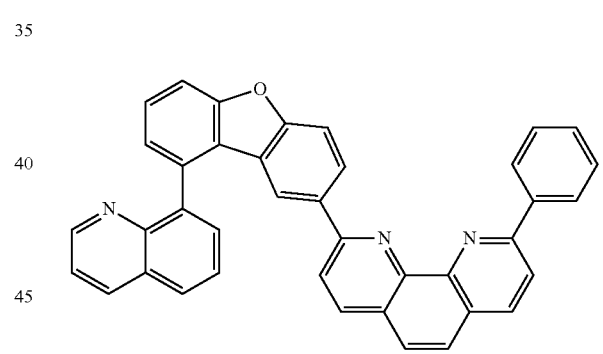
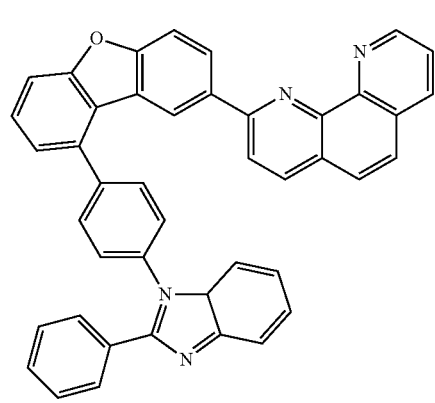
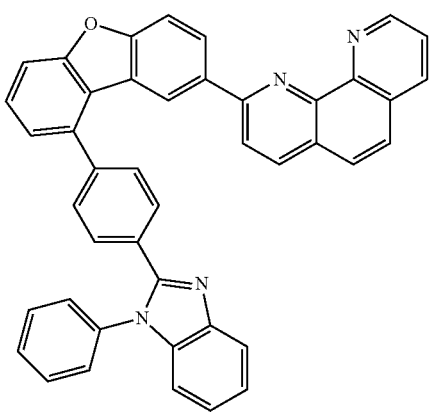

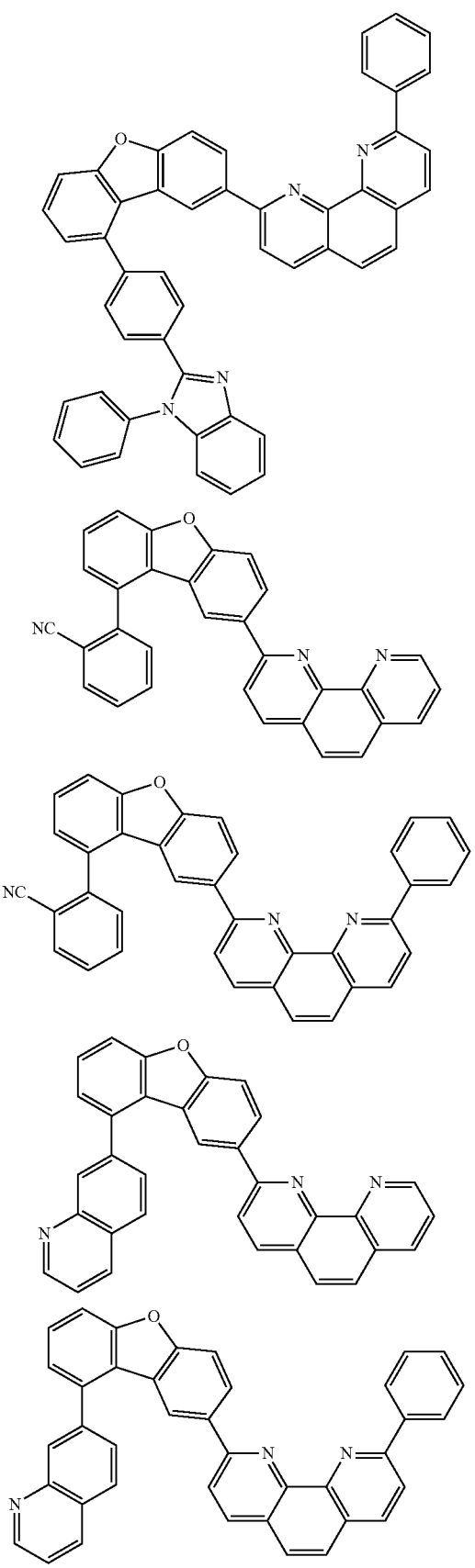
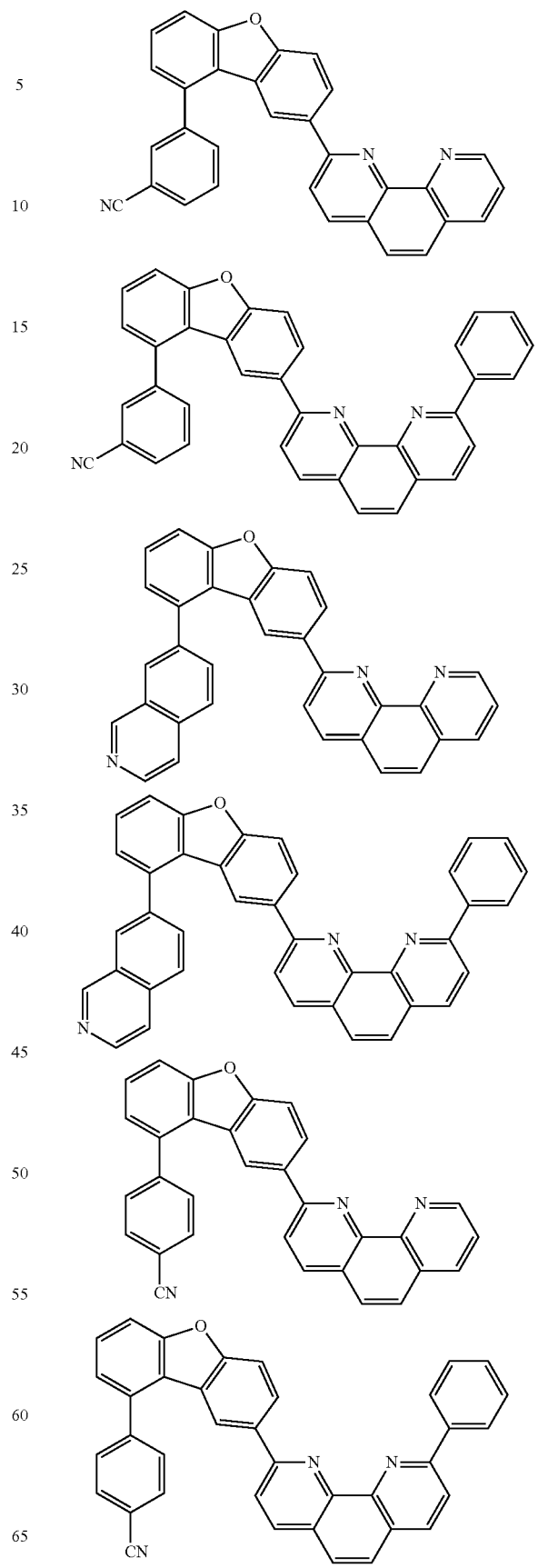

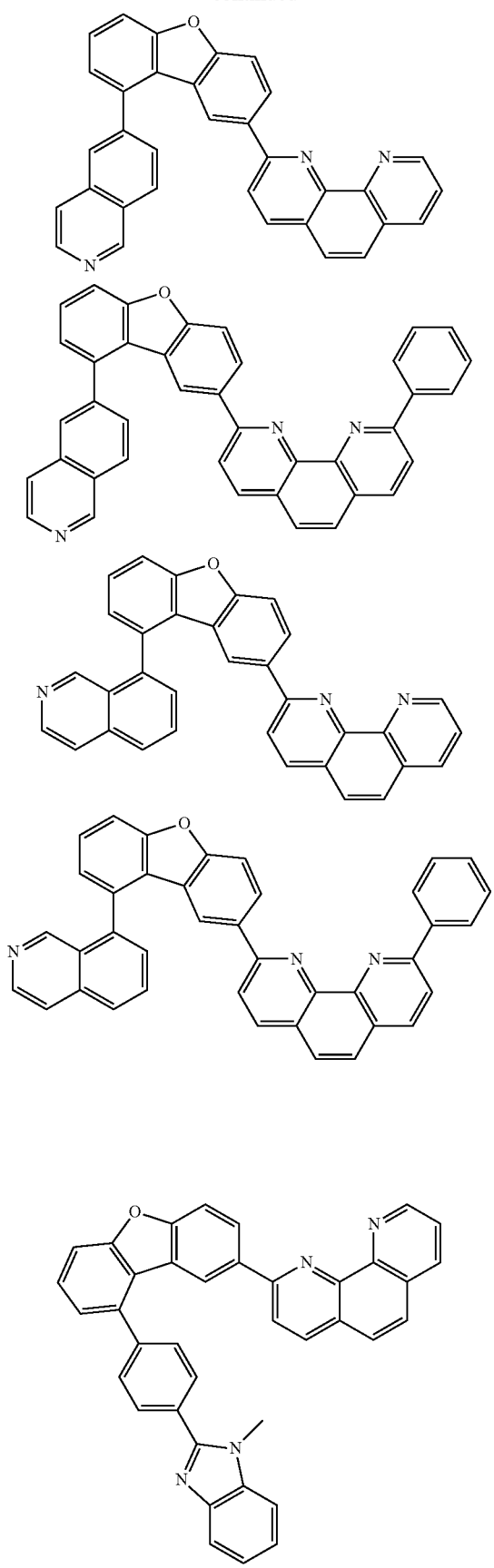
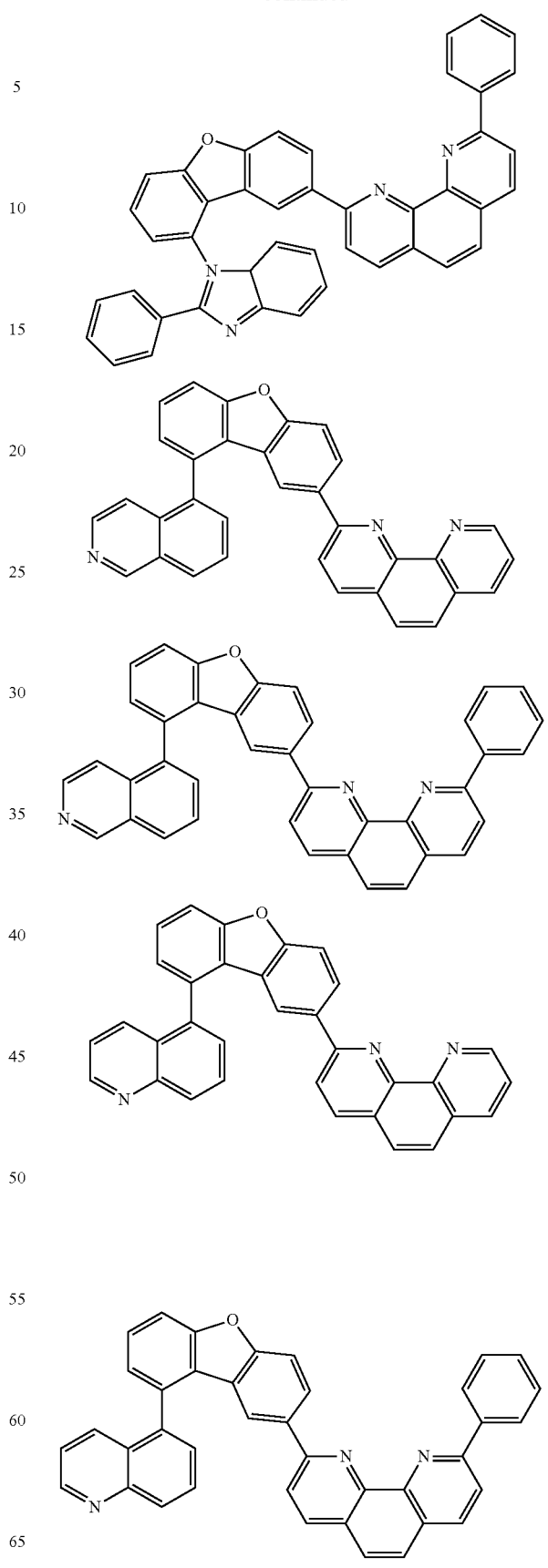

31
-continued
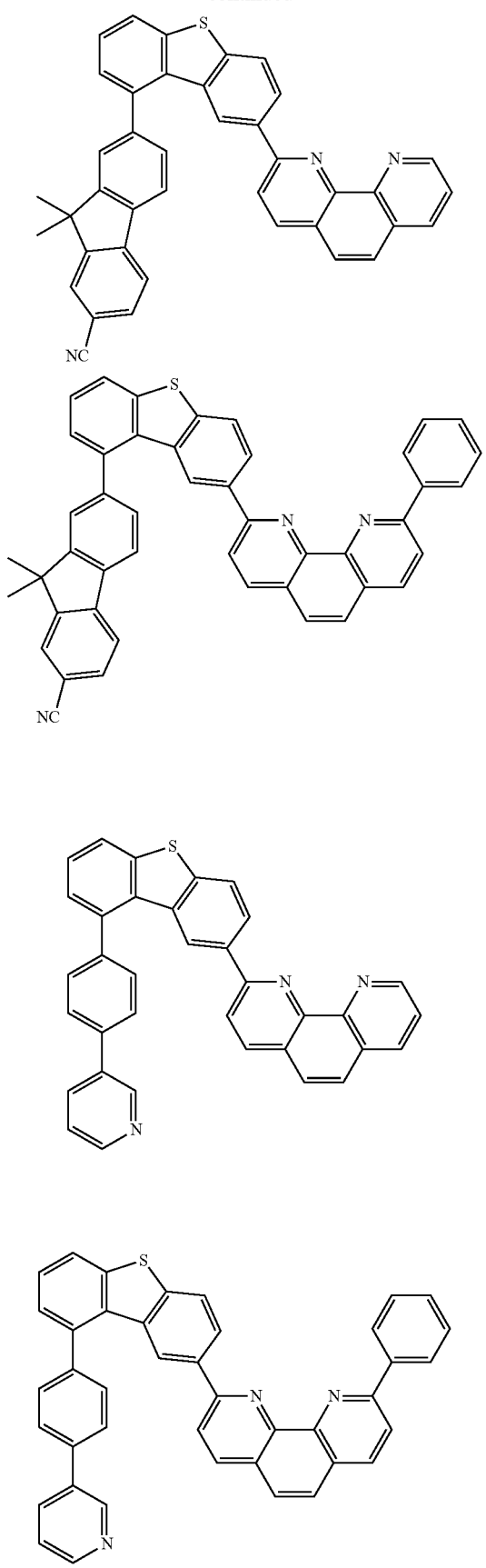
32
-continued
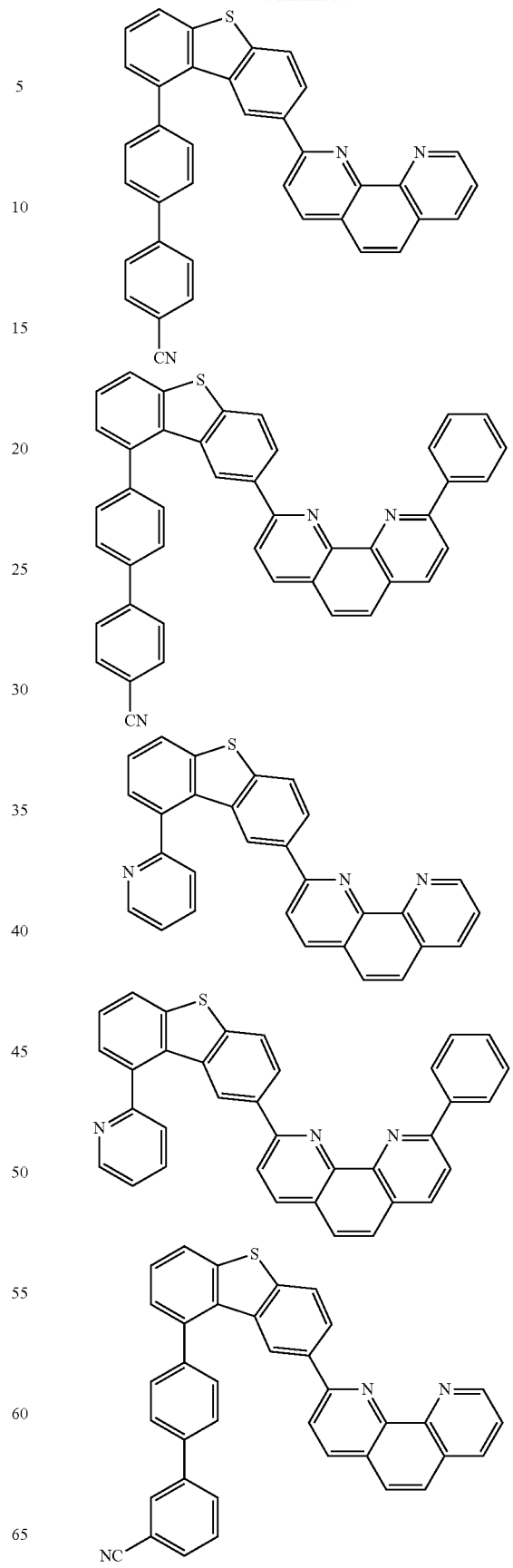

33
-continued
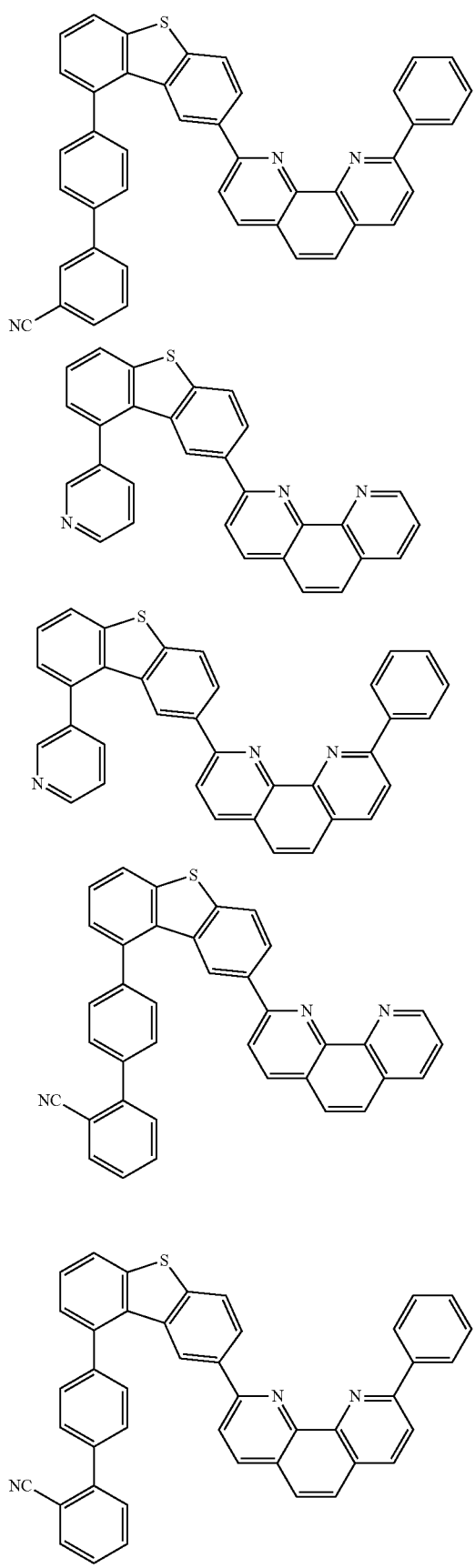
34
-continued
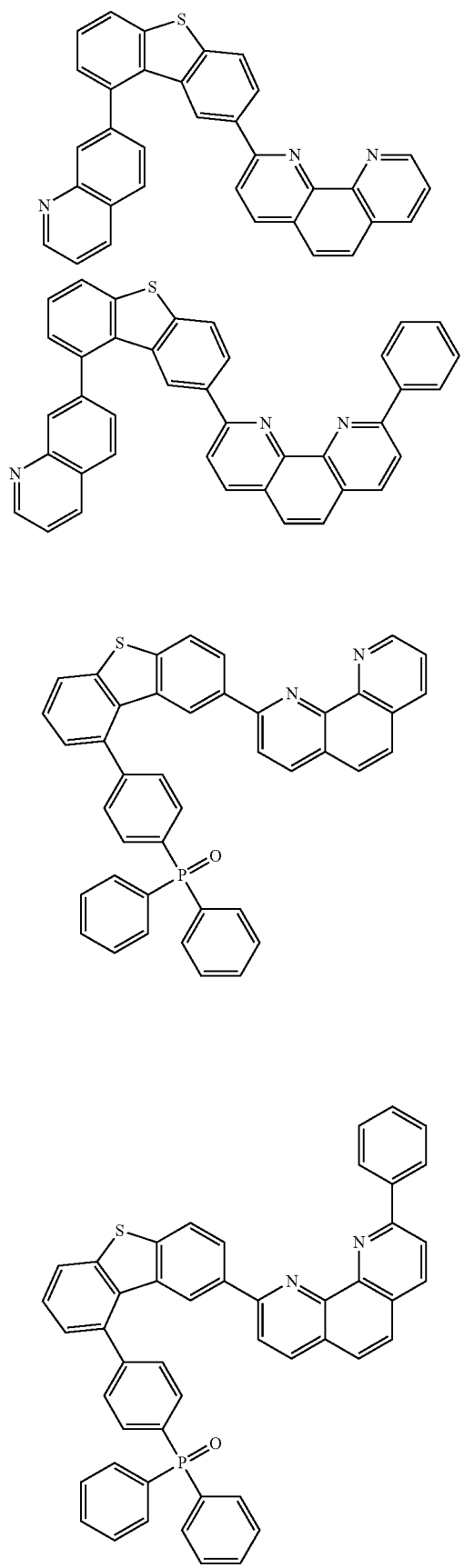

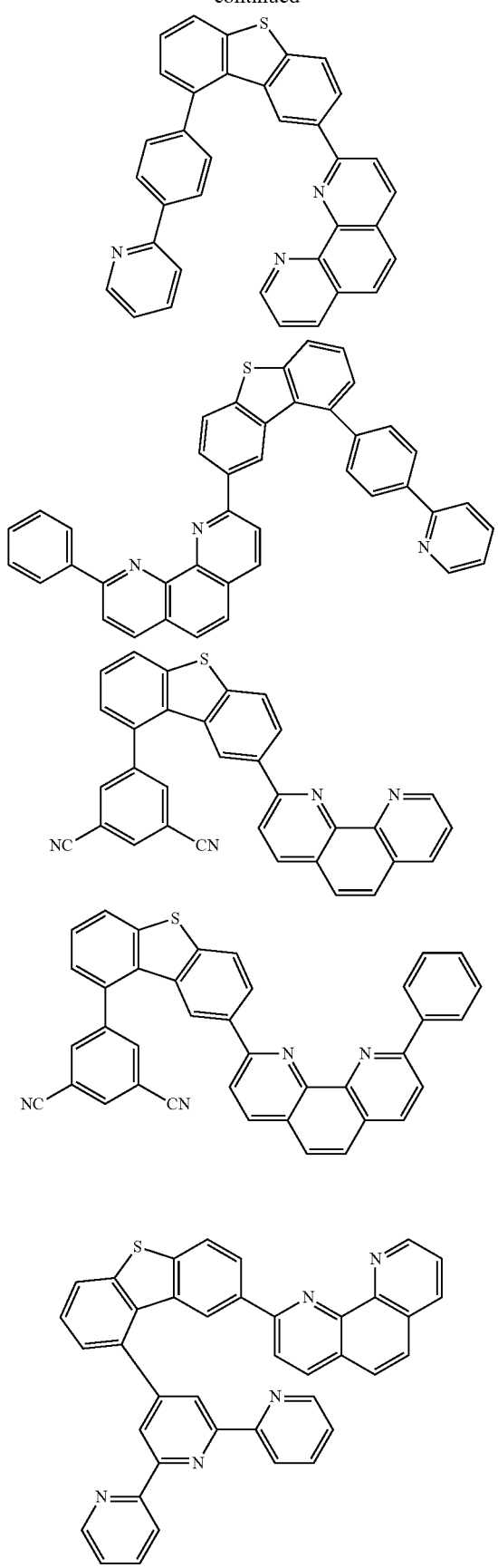
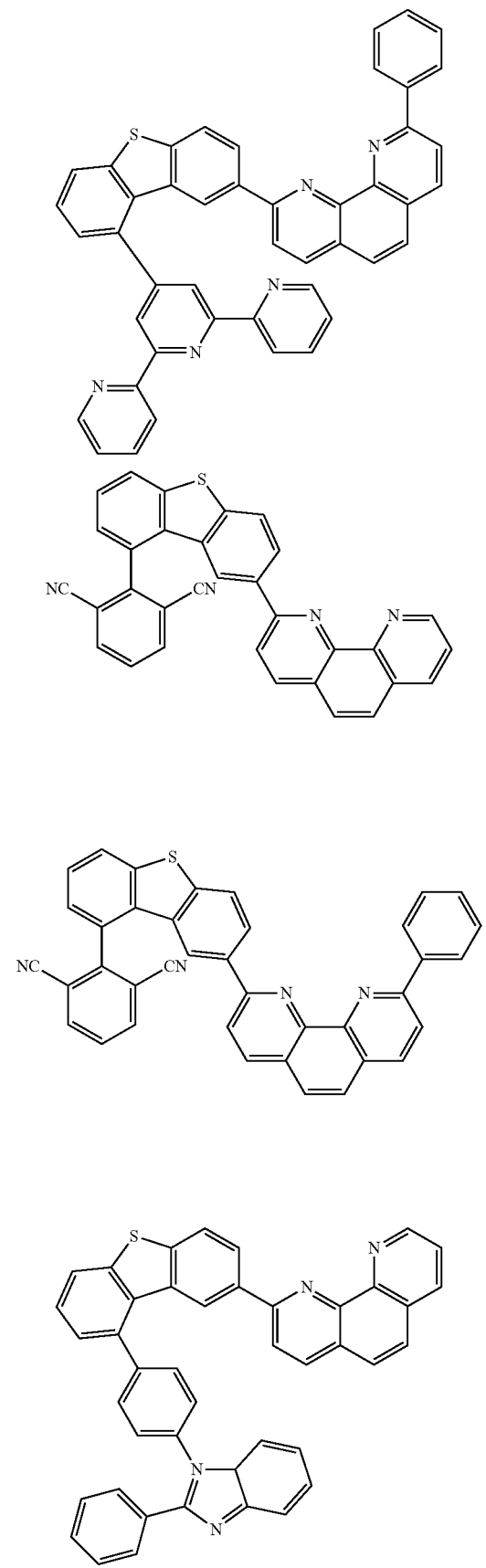

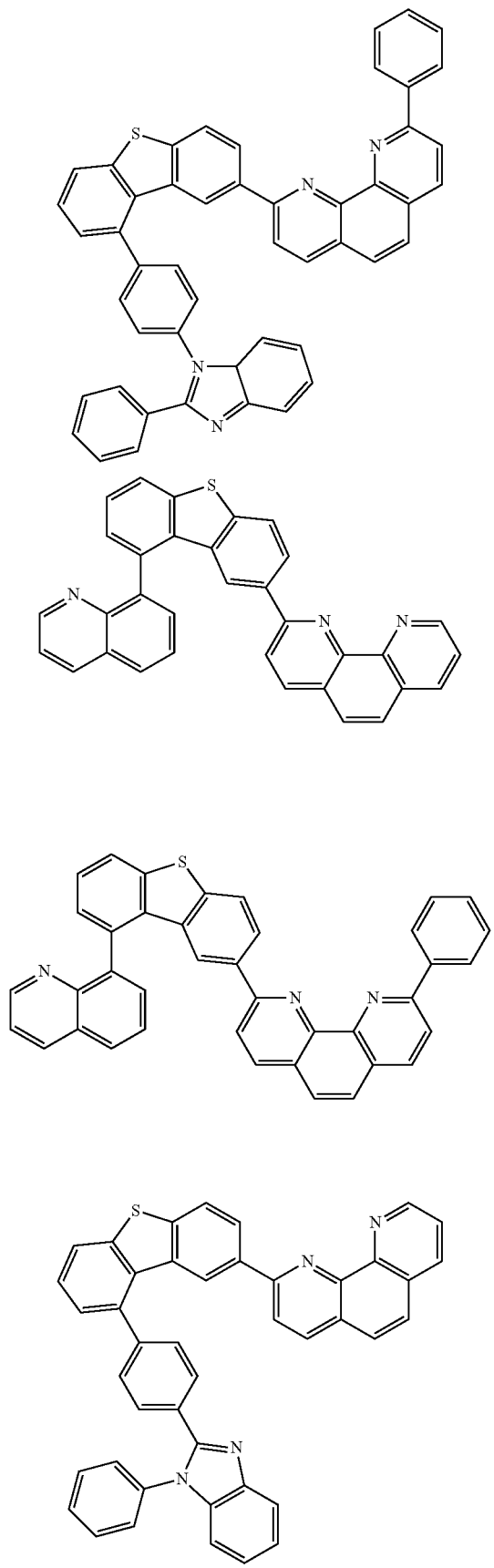
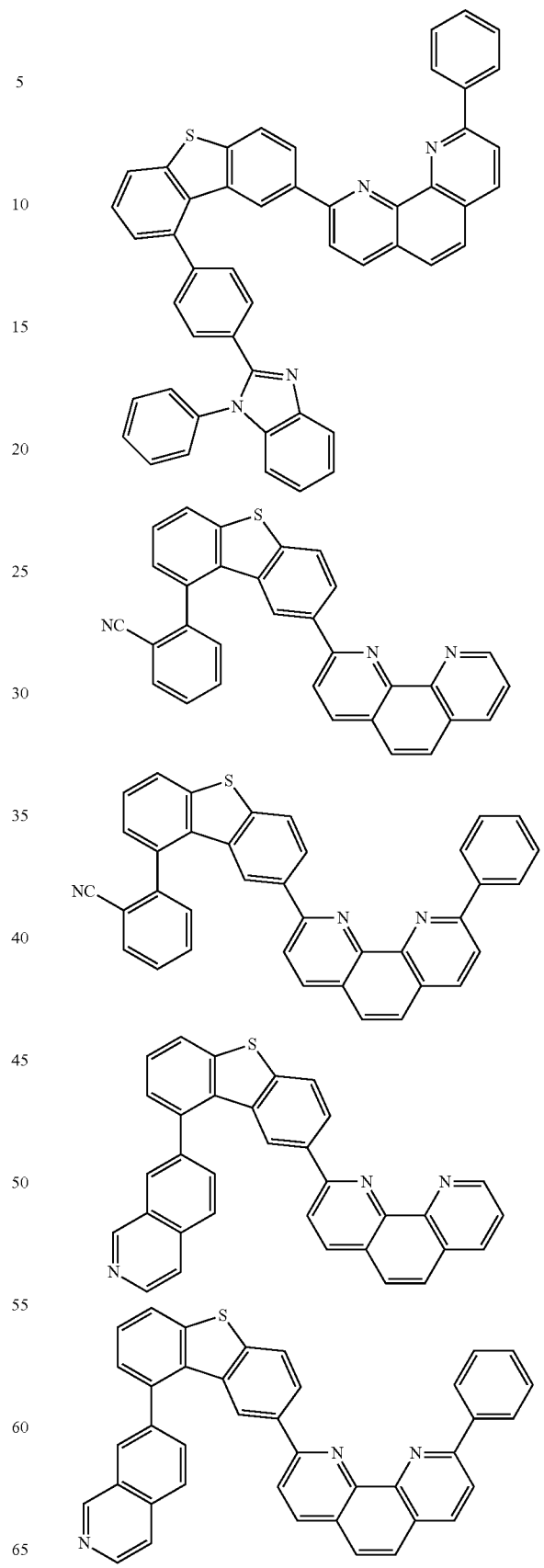

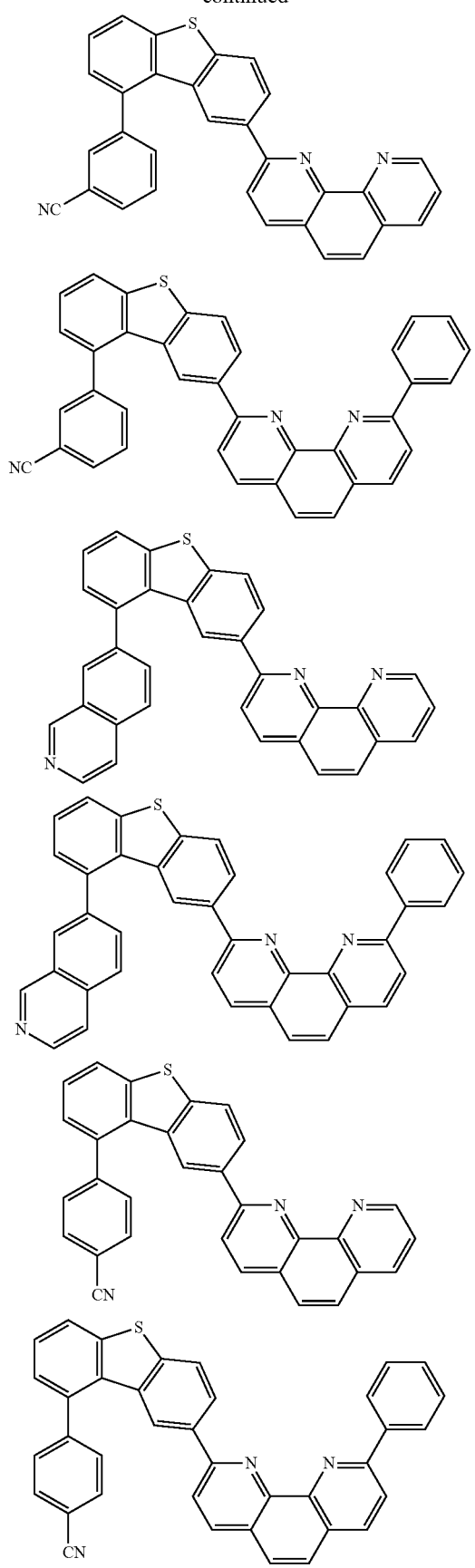
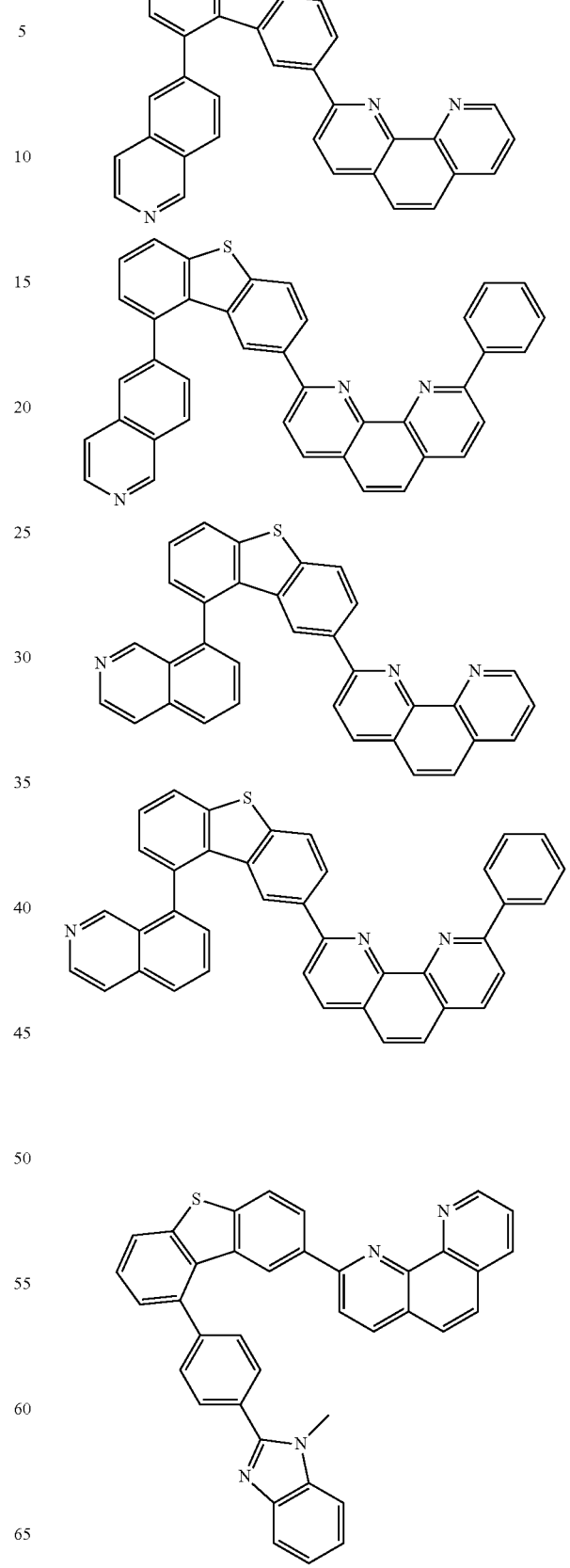

-continued
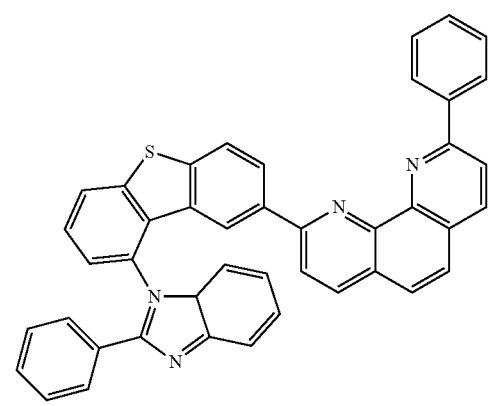
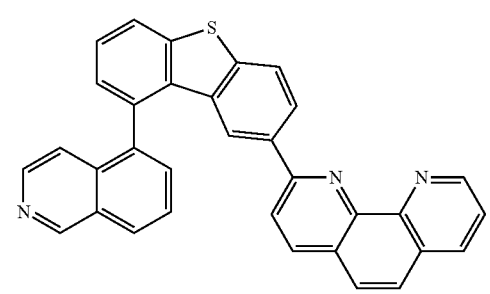
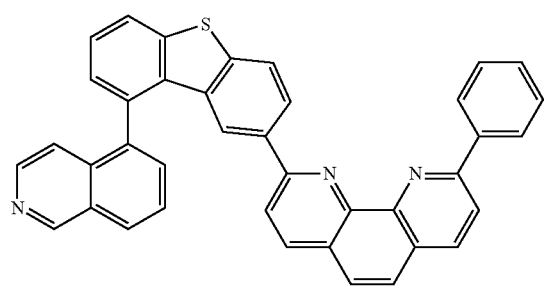
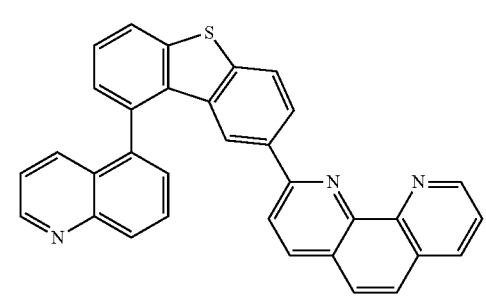
-continued
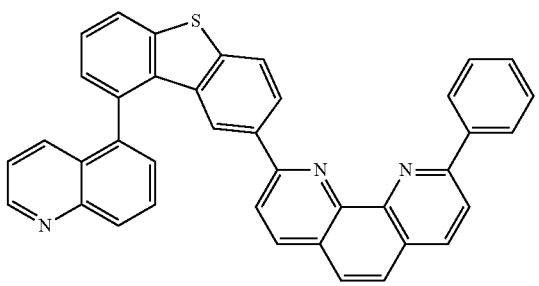
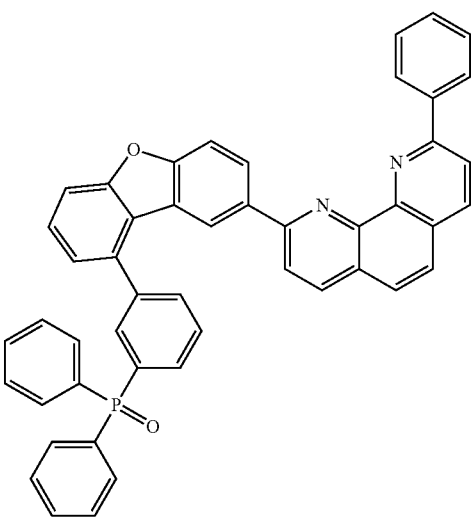
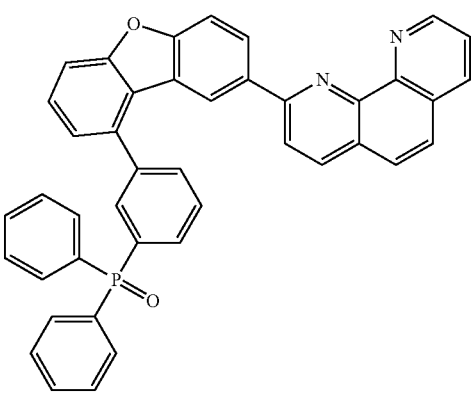
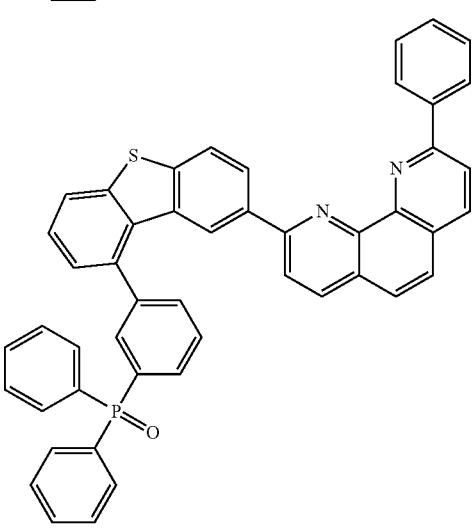

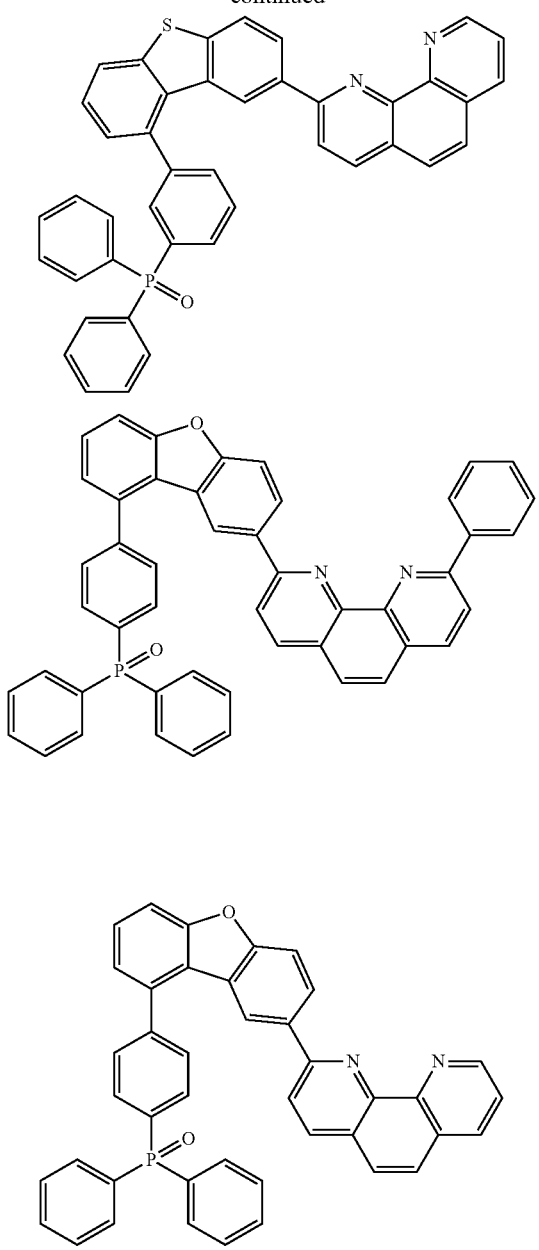

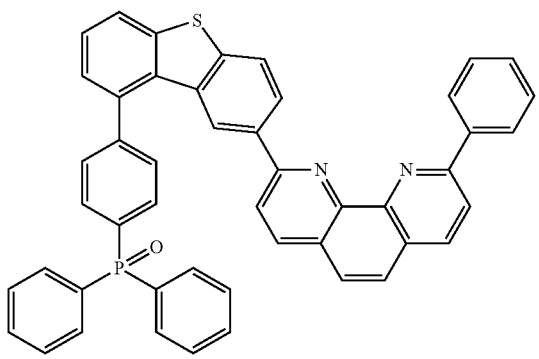

As described above, the compound of Formula 1 includes dibenzofuran or dibenzothiophene as a central structure and has an asymmetric structure in which functional groups of $Ar_1$ and $Ar_2$ are bonded at positions 5 and 9 of the central structure. An electron transport ability, a band gap, an energy level and a thermal property can be more easily controlled through various combinations as compared with the case where the functional groups bonded around benzofuran or dibenzothiophene have a symmetrical structure.

Further, the compound of Formula 1 includes a nitrogen or phosphorus-containing functional group as the functional group $Ar_1$, specifically an aryl group substituted with cyano, pyridinyl or diphenylphosphine oxide group, or a heteroaryl group containing at least one nitrogen, and also includes [1,10]phenanthrolinyl group unsubstituted or substituted with an aryl group having 6 to 20 carbon atoms as the functional group $Ar_2$, and thus can exhibit more advantageous effects in terms of electron injection and transport abilities.

Furthermore, these functional groups $Ar_1$ and $Ar_2$ can be bonded to carbon atoms at positions 5 and 9 of dibenzofuran or dibenzothiophene, respectively, to freely control a three-dimensional structure, thereby exhibiting superior effects in terms of electron injection and transport. Therefore, the organic light emitting device using the same can have a high efficiency, a low driving voltage, a high luminance, a long lifetime, and the like, as compared with the organic light emitting device adopting the compound having a structure in which substituents of the amino group are identical.

The compound of Formula 1 can be prepared by reacting compounds (i) and (ii) in the presence of a palladium-based catalyst such as $Pd(PPh_3)_4$ as shown in the following Reaction Scheme 1 below, but is not limited thereto.

[Reaction Scheme 1]

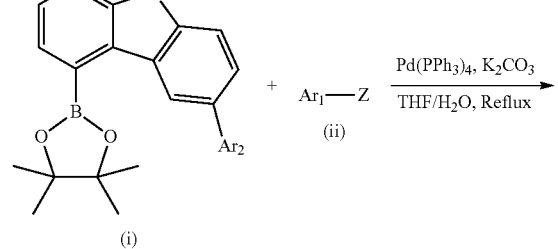

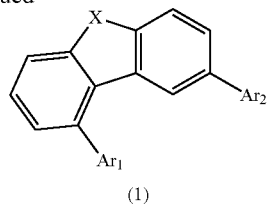

(1)

In the Reaction Scheme 1, X, Ar$_1$, and Ar$_2$ are as defined above, and Z is a halogen group such as Br or the like.

Further, the above reaction can be carried out in a mixture of water and an organic solvent, and a base such as K$_2$CO$_3$ can be further added to improve the reaction efficiency.

The method for preparing the compound of Formula 1 can be further specified in the preparation examples to be described later.

In addition, the present invention provides an organic light emitting device comprising the compound of Formula 1. In one example, the present invention provides an organic light emitting device comprising a first electrode; a second electrode provided at a side opposite to the first electrode; and at least one layer of an organic material layer provided between the first electrode and the second electrode, wherein the at least one layer of the organic material layer includes a compound of Formula 1.

The organic material layer of the organic light emitting device of the present invention can have a single layer structure, but it can have a multilayered structure in which two or more organic material layers are stacked. For example, the organic light emitting device of the present invention can have a structure comprising a hole injection layer, a hole transport layer, a light emitting layer, an electron transport layer, an electron injection layer and the like as the organic material layer. However, the structure of the organic light emitting device is not limited thereto, and it can include a smaller number of organic layers.

Further, the organic material layer can include a hole injection layer, a hole transport layer, or a layer simultaneously performing hole injection and transport, wherein the hole injection layer, the hole transport layer, and the layer simultaneously performing hole injection and transport include a compound of Formula 1.

Further, the organic material layer can include a light emitting layer, wherein the light emitting layer includes a compound of Formula 1.

Further, the organic material layer can include an electron transport layer or an electron injection layer, wherein the electron transport layer or the electron injection layer includes a compound of Formula 1.

Further, the electron transport layer, the electron injection layer and the layer simultaneously performing an electron injection and an electron transport include a compound of Formula 1. In particular, the compound of Formula 1 according to the present invention is excellent in thermal stability, and has deep HOMO levels of 6.0 eV or more, high triplet energies (ET), and hole stability. When the compound of Formula 1 is used for an organic material layer capable of simultaneously performing electron injection and electron transport, an n-type dopant used in the art can be mixed and used.

Further, the organic material layer includes a light emitting layer and an electron transport layer, and the electron transport layer can include a compound of Formula 1.

Further, the organic light emitting device according to the present invention can be a normal type organic light emitting device in which an anode, at least one organic material layer, and a cathode are sequentially stacked on a substrate. Further, the organic light emitting device according to the present invention can be an inverted type organic light emitting device in which a cathode, at least one organic material layer and an anode are sequentially stacked on a substrate. For example, the structure of an organic light emitting device according to an embodiment of the present invention is illustrated in FIGS. 1 and 2.

FIG. 1 shows an example of an organic light emitting device comprising a substrate 1, an anode 2, a light emitting layer 3, and a cathode 4. In such a structure, the compound of Formula 1 can be included in the light emitting layer.

FIG. 2 shows an example of an organic light emitting device comprising a substrate 1, an anode 2, a hole injection layer 5, a hole transport layer 6, a light emitting layer 7, an electron transport layer 8, and a cathode 4. In such a structure, the compound of Formula 1 can be included in at least one layer of the hole injection layer, the hole transport layer, the light emitting layer and the electron transport layer.

The organic light emitting device according to the present invention can be manufactured by materials and methods known in the art, except that at least one layer of the organic material layers includes the compound of Formula 1. In addition, when the organic light emitting device includes a plurality of organic material layers, the organic material layers can be formed of the same material or different materials.

For example, the organic light emitting device according to the present invention can be manufactured by sequentially stacking a first electrode, an organic material layer and a second electrode on a substrate. In this case, the organic light emitting device can be manufactured by depositing a metal, metal oxides having conductivity, or an alloy thereof on the substrate by using a PVD (physical vapor deposition) method such as a sputtering method or an e-beam evaporation method to form the anode, forming an organic material layer including the hole injection layer, the hole transport layer, the light emitting layer, and the electron transport layer thereon, and then depositing a material that can be used as the cathode thereon. In addition to such a method, the organic light emitting device can be manufactured by sequentially depositing a cathode material, an organic material layer and an anode material on a substrate.

In addition, the compound of Formula 1 can be formed into an organic layer by a solution coating method as well as a vacuum deposition method at the time of manufacturing an organic light emitting element. Herein, the solution coating method means a spin coating, a dip coating, a doctor blading, an inkjet printing, a screen printing, a spray method, a roll coating, or the like, but is not limited thereto.

In addition to such a method, the organic light emitting device can be manufactured by sequentially depositing a cathode material, an organic material layer, and an anode material on a substrate (International Publication WO 2003/012890). However, the manufacturing method is not limited thereto.

For example, the first electrode is an anode and the second electrode is a cathode, or the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SnO_2$:Sb; conductive polymers such as poly(3-methyl-thiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

The hole injection layer is a layer for injecting holes from the electrode, and the hole injection material is preferably a compound which has an ability of transporting the holes, a hole injecting effect in the anode and an excellent hole injecting effect to the light emitting layer or the light emitting material, prevents movement of an exciton generated in the light emitting layer to the electron injection layer or the electron injection material, and has an excellent thin film forming ability. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline and polythiophene-based conductive polymer, and the like, but are not limited thereto.

The hole transport layer is a layer that receives holes from a hole injection layer and transports the holes to the light emitting layer. The hole transport material is suitably a material having large mobility to the holes, which can receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The light emitting material is a material capable of emitting light in the visible light region by combining holes and electrons respectively transported from the hole transport layer and the electron transport layer, and having good quantum efficiency for fluorescence or phosphorescence. Specific examples include 8-hydroxy-quinoline aluminum complex ($Alq_3$); carbazole-based compounds; dimerized styryl compounds; BAlq; 10-hydroxybenzoquinoline-metal compounds; benzoxazole, benzothiazole and benzimidazole-based compounds; poly(p-phenylenevinylene) (PPV)-based polymers; spiro compounds; polyfluorene, rubrene, and the like, but are not limited thereto.

The light emitting layer can include a host material and a dopant material. The host material can be a fused aromatic ring derivative, a heterocycle-containing compound or the like. Specific examples of the fused aromatic ring derivatives include anthracene derivatives, pyrene derivatives, naphthalene derivatives, pentacene derivatives, phenanthrene compounds, and fluoranthene compounds. Examples of heterocyclic-containing compounds include carbazole derivatives, dibenzofuran derivatives, ladder-type furan compounds, pyrimidine derivatives, and the like, but are not limited thereto.

Examples of the dopant material include an aromatic amine derivative, a styrylamine compound, a boron complex, a fluoranthene compound, a metal complex, and the like. Specific examples of the aromatic amine derivatives include substituted or unsubstituted fused aromatic ring derivatives having an arylamino group, examples thereof include pyrene, anthracene, chrysene, and periflanthene having the arylamino group, and the like, the styrylamine compound is a compound where at least one arylvinyl group is substituted in substituted or unsubstituted arylamine, in which one or more substituent groups selected from the group consisting of an aryl group, a silyl group, an alkyl group, a cycloalkyl group, and an arylamino group are substituted or unsubstituted.

Specific examples thereof include styrylamine, styryldiamine, styryltriamine, styryltetramine, and the like, but are not limited thereto. Further, examples of the metal complex include an iridium complex, a platinum complex, and the like, but are not limited thereto. The content of the dopant material can be from 1% to 99% relative to the content of the host material of the light emitting layer.

The electron transport layer is a layer receiving the electrons from the electron injection layer and transporting the electrons to the light emitting layer, the electron transport material is a material that can receive the electrons well from the cathode and transport the electrons to the light emitting layer, and a material having large mobility to the electrons is suitable. Specific examples thereof include an 8-hydroxyquinoline Al complex; a complex including $Alq_3$; an organic radical compound; a hydroxyflavone-metal complex, and the like, but are not limited thereto. The electron transport layer can be used together with a predetermined desired cathode material as used according to the prior art. Particularly, an example of an appropriate cathode material is a general material having the low work function and followed by an aluminum layer or a silver layer. Specific examples thereof include cesium, barium, calcium, ytterbium, and samarium, and each case is followed by the aluminum layer or the silver layer.

The electron injection layer is a layer injecting the electrons from the electrode, and a compound which has an ability of transporting the electrons, an electron injecting effect from the cathode, and an excellent electron injecting effect to the light emitting layer or the light emitting material, prevents movement of an exciton generated in the light emitting layer to the hole injection layer, and has an excellent thin film forming ability is preferable. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone, and the like, and its derivative, a metal complex compound, a nitrogen-containing 5-membered cycle derivative, and the like, but are not limited thereto.

Examples of the metal complex compound include 8-hydroxyquinolinato lithium, bis(8-hydroxyquinolinato)-zinc, bis(8-hydroxyquinolinato)copper, bis(8-hydroxy-quinolinato)manganese, tris(8-hydroxyquinolinato)-aluminum, tris (2-methyl-8-hydroxyquinolinato)aluminum, tris(8-hydroxyquinolinato)gallium, bis(10-hydroxy-benzo[h]quinolinato) beryllium, bis(10-hydroxy-benzo[h]quinolinato)zinc, bis(2-methyl-8-quinolinato)-chlorogallium, bis(2-methyl-8-quinolinato) (o-cresolato)gallium, bis(2-methyl-8- quinolinato) (1-naphtholato)aluminum, bis(2-methyl-8-quinolinato) (2-naphtholato)gallium, and the like, but are not limited thereto.

The organic light emitting device according to the present invention can be a front side emission type, a back side emission type, or a double side emission type according to the used material.

In addition, the compound of Formula 1 can be included in an organic solar cell or an organic transistor in addition to an organic light emitting device.

The preparation of the compound of Formula 1 and the organic light emitting device comprising the same will be described in detail in the following examples. However, these examples are presented for illustrative purposes only, and the scope of the present invention is not limited thereto.

Preparation Example 1

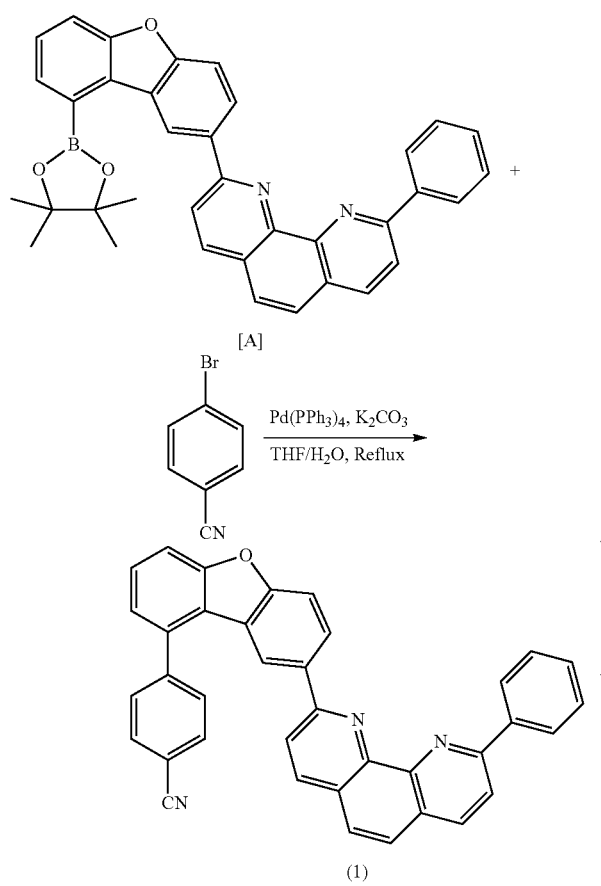

(1)

In a 500 ml round bottom flask, Compound A (20.00 g, 32.12 mmol) and 4-bromobenzonitrile (6.61 g, 32.12 mmol) were completely dissolved in 300 ml of tetrahydrofuran (THF) under nitrogen atmosphere, and then 2M aqueous potassium carbonate solution (150 ml) was added thereto. Tetrakis(triphenylphosphine)-palladium (Pd(PPh$_3$)$_4$) (1.11 g, 0.96 mmol) was added and the mixture was heated and stirred for 3 hours. The temperature was lowered to room temperature (23±5° C.), and the aqueous layer was removed, dried over anhydrous magnesium sulfate, concentrated under reduced pressure, and recrystallized from ethyl acetate (180 ml) to prepare Compound 1 (11.9 g, 59%).

MS [M+H]$^+$=523

Preparation Example 2

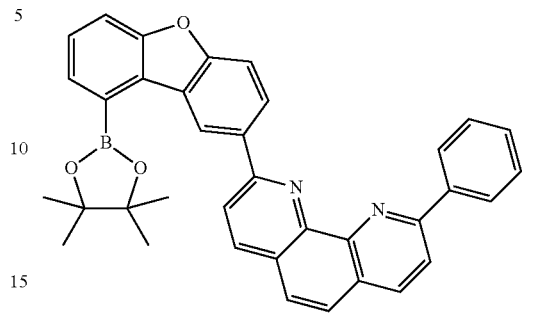

[A]

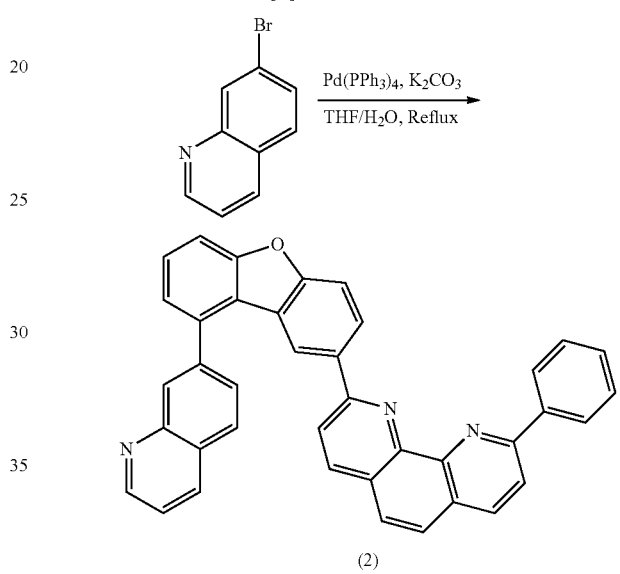

(2)

Compound 2 was prepared in the same manner as in Preparation Example 1, except that 7-bromoquinoline was used instead of the compound 4-bromobenzonitrile in Preparation Example 1.

MS [M+H]$^+$=549

Preparation Example 3

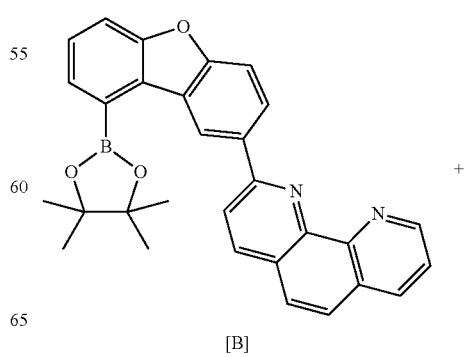

[B]

-continued

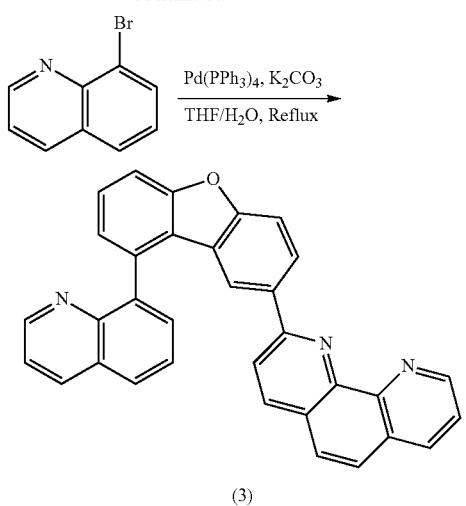

(3)

In a 500 ml round bottom flask, Compound B (22.90 g, 38.34 mmol) and 8-bromoquinoline (7.97 g, 38.34 mmol) were completely dissolved in 300 ml of tetrahydrofuran under nitrogen atmosphere, and then 2M aqueous potassium carbonate solution (150 ml) was added thereto. Tetrakis (triphenylphosphine)palladium (1.32 g, 1.15 mmol) was added and the mixture was heated and stirred for 3 hours. The temperature was lowered to room temperature (23±5° C.), and the aqueous layer was removed, dried over anhydrous magnesium sulfate, concentrated under reduced pressure, and recrystallized from ethyl acetate (180 ml) to prepare Compound 3 (16.5 g, 63%).

MS [M+H]$^+$=473

Preparation Example 4

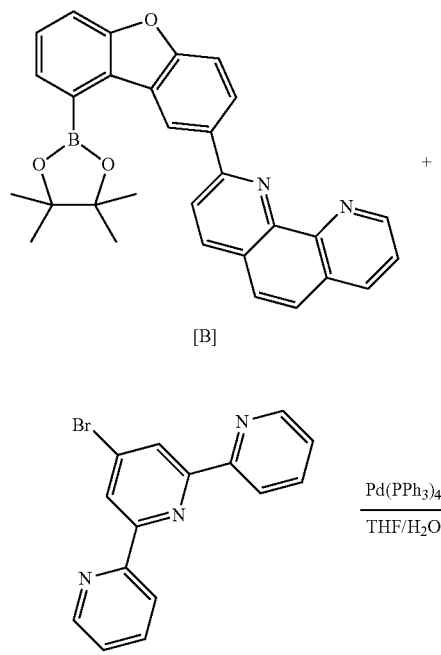

-continued

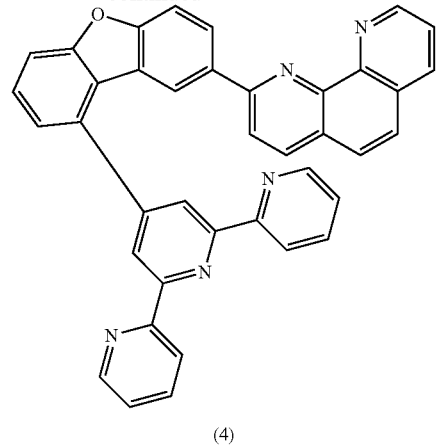

(4)

Compound 4 was prepared in the same manner as in Preparation Example 3, except that 4'-bromo-2,2':6', 2"-terpyridine was used instead of 8-bromoquinoline in Preparation Example 3.

MS [M+H]=577

Preparation Example 5

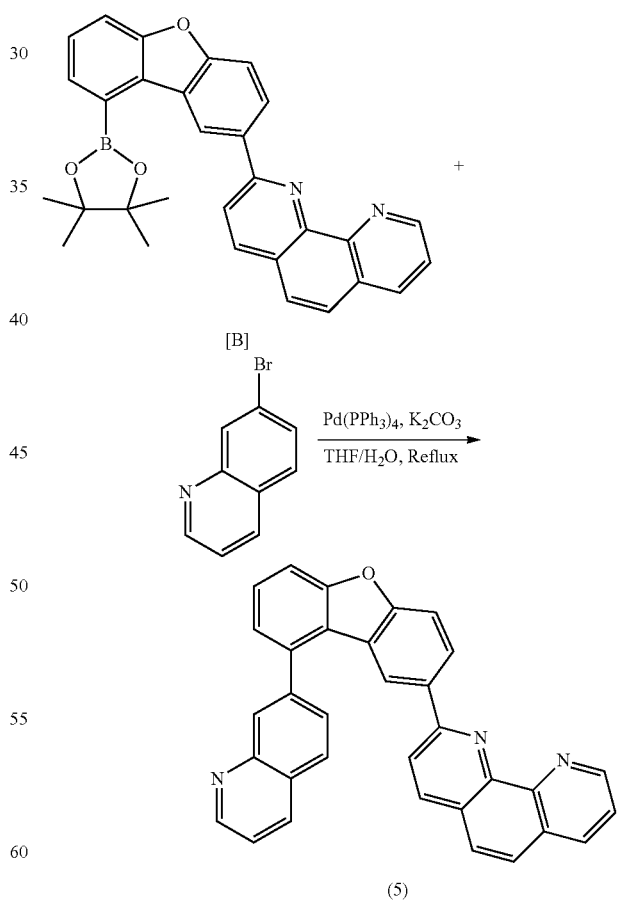

(5)

Compound 5 was prepared in the same manner as in Preparation Example 3, except that 7-bromoquinoline was used instead of 8-bromoquinoline in Preparation Example 3.

MS [M+H]$^+$=473

Preparation Example 6

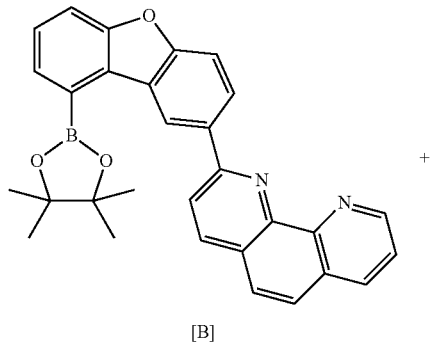

[B]

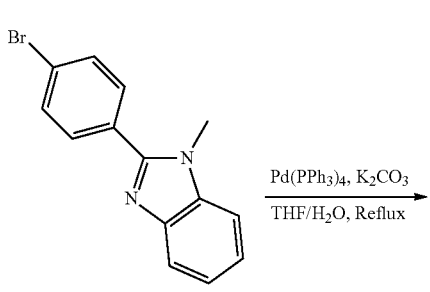

Pd(PPh₃)₄, K₂CO₃
THF/H₂O, Reflux

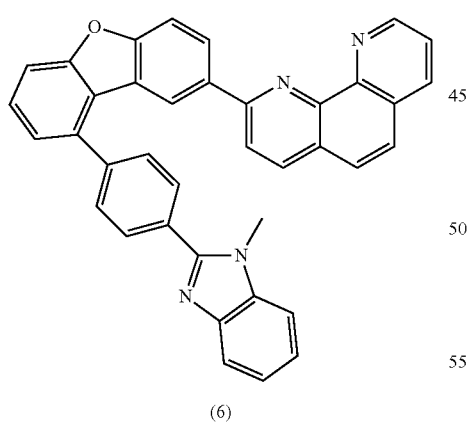

(6)

Compound 6 was prepared in the same manner as in Preparation Example 3, except that 2-(4-bromophenyl)-1-methyl-1H-benzo[d]imidazole was used instead of 8-bromoquinoline 8 bromopyridine in Preparation Example 3.

MS [M+H]⁺=552

Preparation Example 7

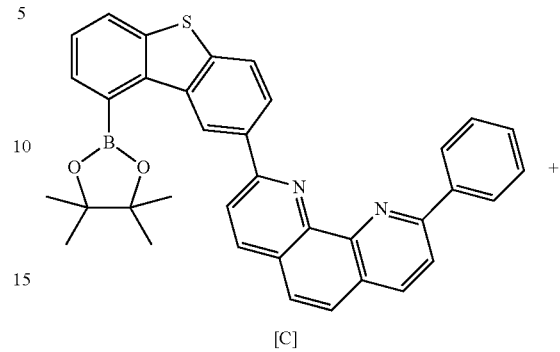

[C]

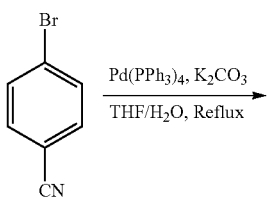

Pd(PPh₃)₄, K₂CO₃
THF/H₂O, Reflux

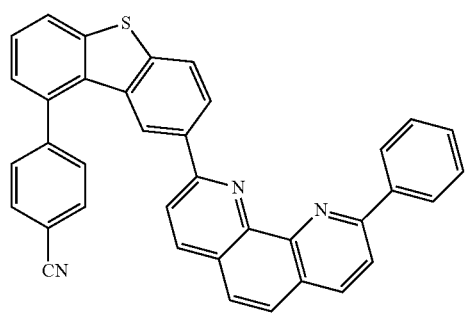

(7)

In a 500 ml round bottom flask, Compound C (20.00 g, 32.12 mmol) and 4-bromobenzonitrile (6.61 g, 32.12 mmol) were completely dissolved in 300 ml of tetrahydrofuran (THF) under nitrogen atmosphere, and then 2M aqueous potassium carbonate solution (150 ml) was added thereto. Tetrakis(triphenylphosphine)-palladium (Pd(PPh₃)₄) (1.11 g, 0.96 mmol) was added and the mixture was heated and stirred for 3 hours. The temperature was lowered to room temperature (23±5° C.), and the aqueous layer was removed, dried over anhydrous magnesium sulfate, concentrated under reduced pressure, and recrystallized from ethyl acetate (180 ml) to prepare Compound 7 (11.9 g, 59%).

MS [M+H]⁺=539

Preparation Example 8

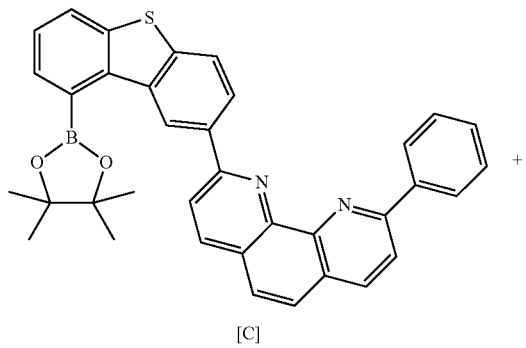

[C]

Preparation Example 9

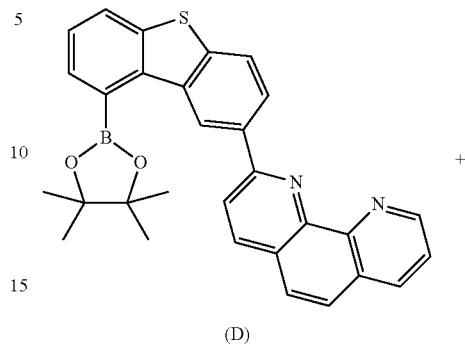

(D)

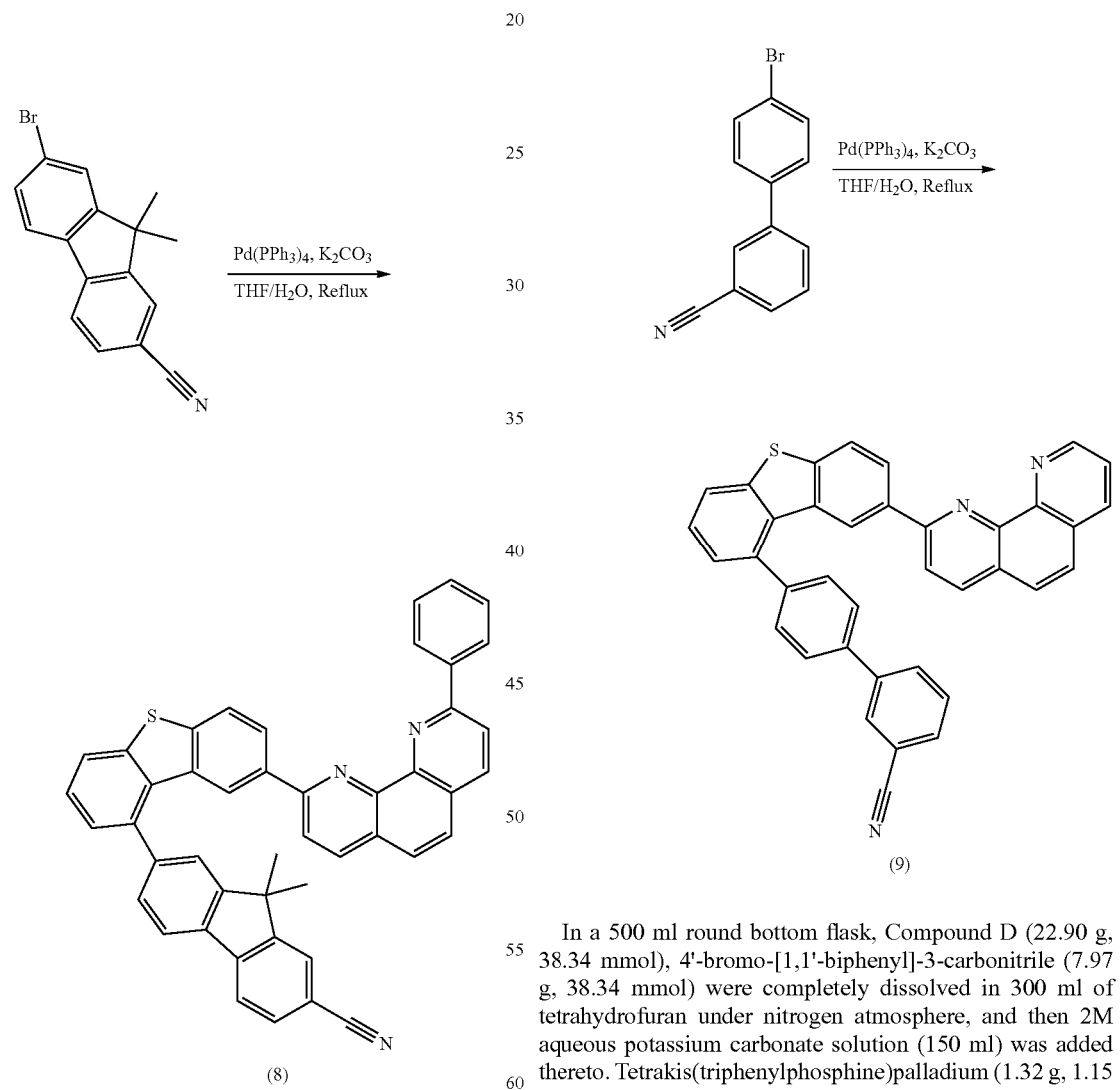

Compound 8 was prepared in the same manner as in Preparation Example 7, except that 7-bromo-9,9-dimethyl-9H-fluorene-2-carbonitrile was used instead of 4-bromobenzonitrile in Preparation Example 7.

MS [M+H]$^+$=655

In a 500 ml round bottom flask, Compound D (22.90 g, 38.34 mmol), 4'-bromo-[1,1'-biphenyl]-3-carbonitrile (7.97 g, 38.34 mmol) were completely dissolved in 300 ml of tetrahydrofuran under nitrogen atmosphere, and then 2M aqueous potassium carbonate solution (150 ml) was added thereto. Tetrakis(triphenylphosphine)palladium (1.32 g, 1.15 mmol) was added and the mixture was heated and stirred for 3 hours. The temperature was lowered to room temperature (23±5° C.), and the aqueous layer was removed, dried over anhydrous magnesium sulfate, concentrated under reduced pressure, and recrystallized from ethyl acetate (180 ml) to prepare Compound 9 (16.5 g, 63%).

MS [M+H]$^+$=539

Preparation Example 10

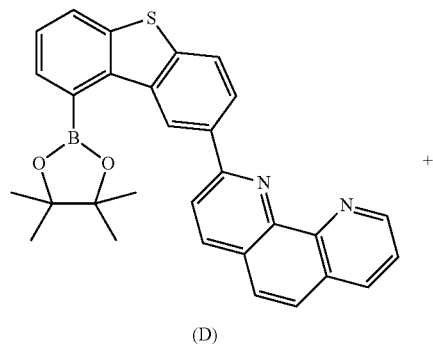

(D)

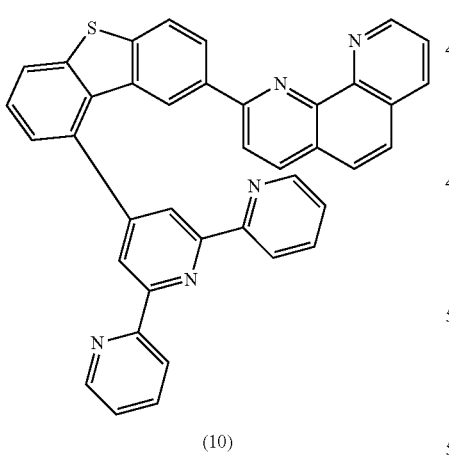

(10)

Compound 10 was prepared in the same manner as in Preparation Example 9, except that 4'-bromo-2,2': 6',2''-terpyridine was used instead of 4'-bromo-[1,1'-biphenyl]-3-carbonitrile in Preparation Example 9.

MS [M+H]$^+$=593

Preparation Example 11

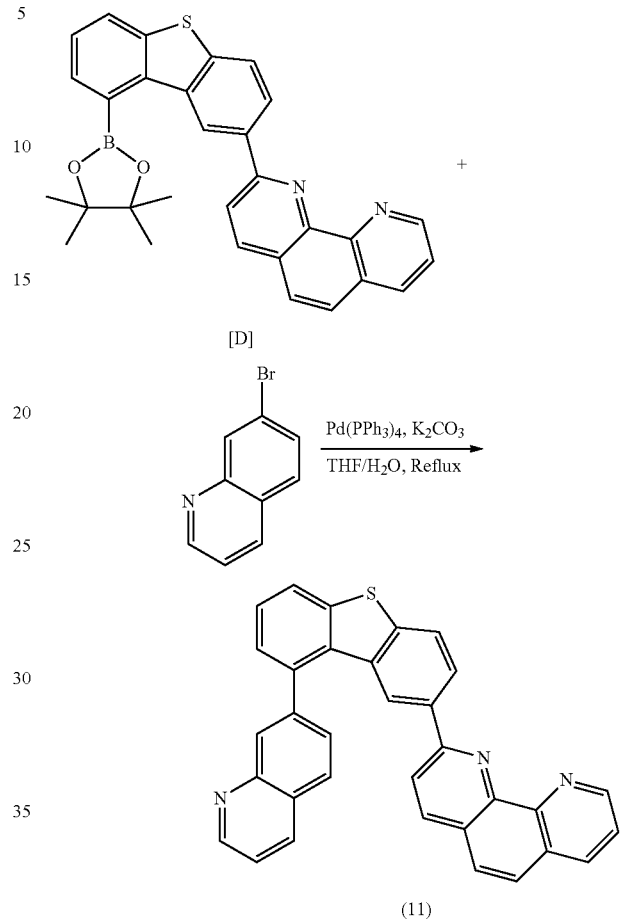

Compound 11 was prepared in the same manner as in Preparation Example 9, except that 7-bromoquinoline was used instead of 4'-bromo-[1,1'-biphenyl]-3-carbonitrile in Preparation Example 9.

MS [M+H]$^+$=489

Preparation Example 12

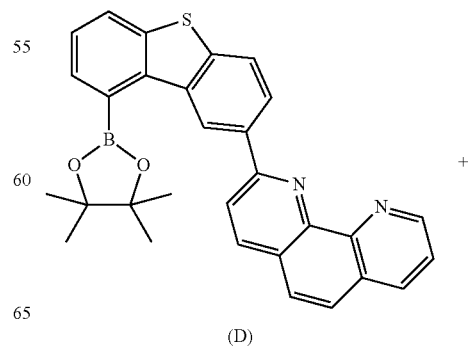

(D)

-continued

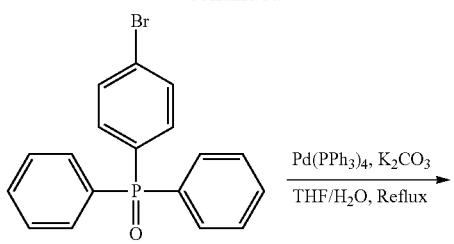

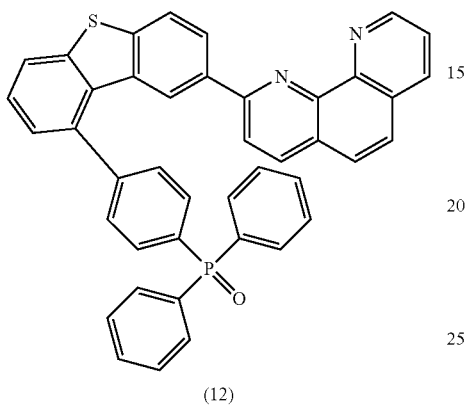

(12)

Compound 12 was prepared in the same manner as in Preparation Example 9, except that (4-bromophenyl)-diphenylphosphine oxide was used instead of 4'-bromo-[1,1'-biphenyl]-3-carbonitrile in Preparation Example 9.

MS [M+H]⁺=638

Examples 1-1

A glass substrate on which a thin film of ITO (indium tin oxide) was coated in a thickness of 1,000 Å was put into distilled water containing the detergent dissolved therein and washed by the ultrasonic wave. In this case, the used detergent was a product commercially available from Fischer Co. and the distilled water was one which had been twice filtered by using a filter commercially available from Millipore Co. The ITO was washed for 30 minutes, and ultrasonic washing was then repeated twice for 10 minutes by using distilled water. After the washing with distilled water was completed, the substrate was ultrasonically washed with isopropyl alcohol, acetone, and methanol solvent, and dried, after which it was transported to a plasma cleaner. Then, the substrate was cleaned with oxygen plasma for 5 minutes, and then transferred to a vacuum evaporator.

On the ITO transparent electrode thus prepared, a compound of Formula [HI-A] below was thermally vacuum-deposited in a thickness of 600 Å to form a hole injection layer. Hexanitrile hexaazatriphenylene of Formula [HAT] below (50 Å) and a compound of Formula [HT-A] below (600 Å) were sequentially vacuum-deposited on the hole injection layer to form a hole transport layer.

Then, compounds of Formulas [BH3] and [BH2D] below were vacuum-deposited at a weight ratio of 25:1 on the hole transport layer in a thickness of 200 Å to form a light emitting layer.

The Compound 1 prepared in Preparation Example 1 and a compound of Formula [LiQ] (lithium quinolate) were vacuum-deposited at a weight ratio of 1:1 on the light emitting layer to form an electron injection and transport layer with a thickness of 350 Å. Lithium fluoride (LiF) (10 Å) and aluminum (1,000 Å) were sequentially deposited on the electron injection and transport layer to form a cathode.

In the above process, the vapor deposition rate of the organic material was maintained at 0.4 to 0.9 Å/sec, the vapor deposition rate of lithium fluoride of the cathode was maintained at 0.3 Å/sec, the vapor deposition rate of aluminum was maintained at 2 Å/sec, and the degree of vacuum during vapor deposition was maintained at $1\times10^{-7}$ to $5\times10^{-8}$ torr to manufacture an organic light emitting device.

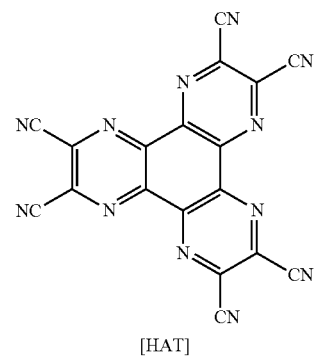

[HAT]

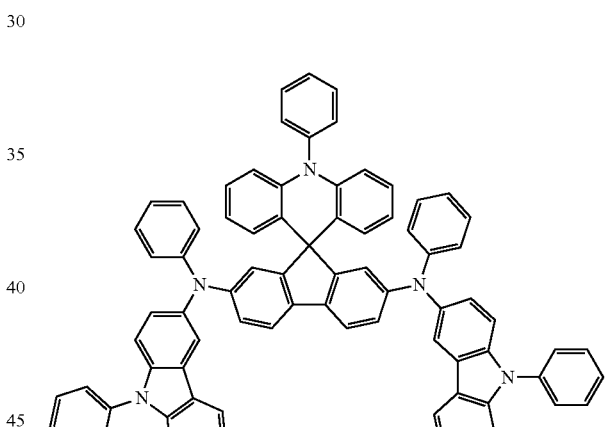

[HI-A]

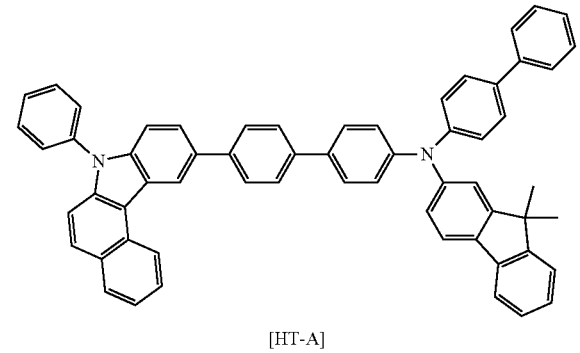

[HT-A]

-continued

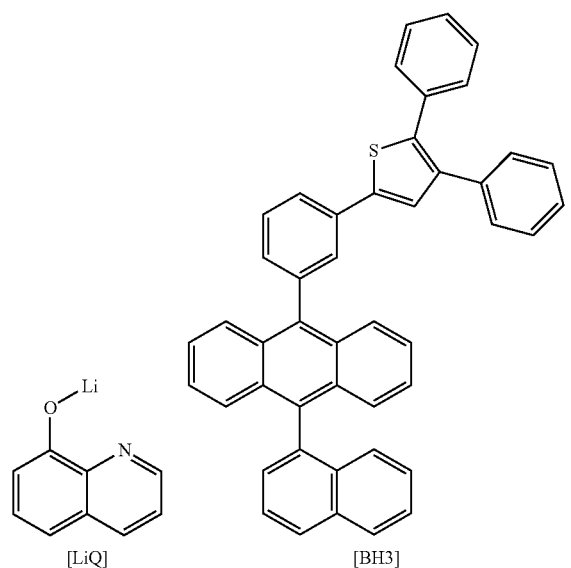
[LiQ]    [BH3]

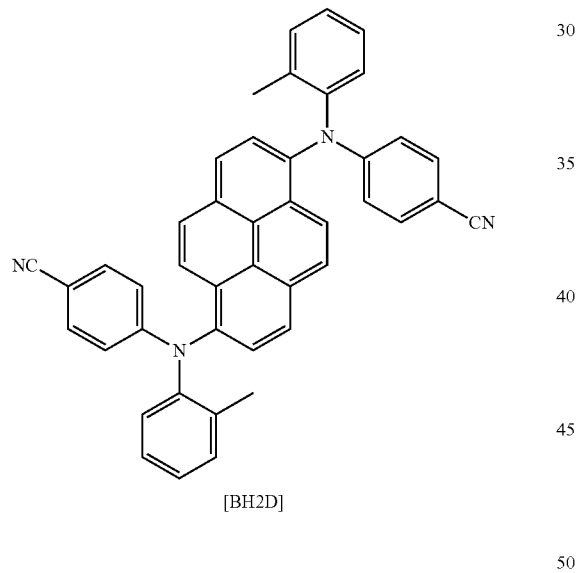
[BH2D]

Examples 1-2 to 1-12

The organic light emitting device was manufactured in the same manner as in Example 1-1, except that the compounds shown in Table 1 below were used instead of the compound 1 in Example 1-1.

Comparative Examples 1-1 to 1-5

The organic light emitting devices were manufactured in the same manner as in Example 1-1, except that the compounds (a), (b), (c), (d), or (e) having the following structures shown in Table 1 below were used instead of the compound 1 in Example 1-1.

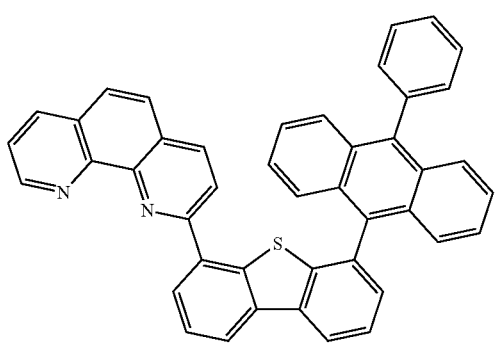
(a)

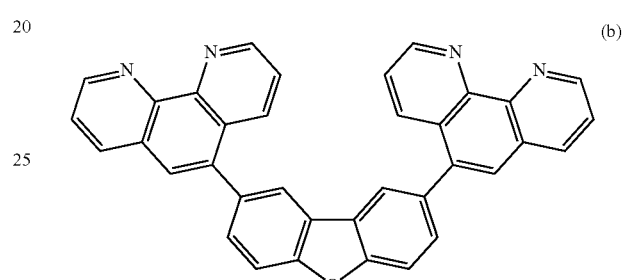
(b)

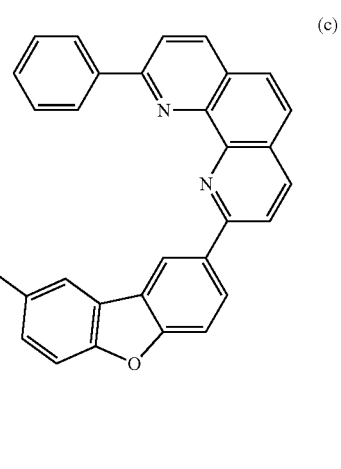
(c)

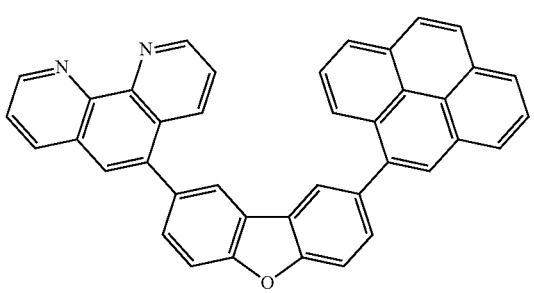
(d)

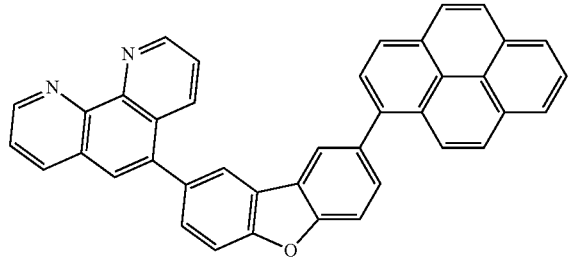

(e)

Experimental Example 1

The driving voltage and light emitting efficiency were measured at the current density of 10 mA/cm² for the organic light emitting devices manufactured in the Examples 1-1 to 1-12 and Comparative Examples 1-1 to 1-5, and the time ($T_{90}$) at which the luminance became 90% relative to the initial luminance at the current density of 20 mA/cm² was measured. The results are shown in Table 1 below.

TABLE 1

| | Compound | Voltage (V@10 mA/cm²) | Efficiency (cd/A@10 mA/cm²) | Color coordinate (x, y) | Lifetime(h) $T_{90}$ at 20 mA/cm² |
|---|---|---|---|---|---|
| Example 1-1 | 1 | 4.54 | 5.47 | (0.142, 0.097) | 167 |
| Example 1-2 | 2 | 4.54 | 5.47 | (0.142, 0.096) | 167 |
| Example 1-3 | 3 | 4.63 | 5.56 | (0.142, 0.099) | 148 |
| Example 1-4 | 4 | 4.76 | 5.41 | (0.142, 0.096) | 197 |
| Example 1-5 | 5 | 4.65 | 5.55 | (0.142, 0.096) | 146 |
| Example 1-6 | 6 | 4.55 | 5.70 | (0.142, 0.099) | 156 |
| Example 1-7 | 7 | 4.53 | 5.66 | (0.142, 0.096) | 158 |
| Example 1-8 | 8 | 4.54 | 5.47 | (0.142, 0.096) | 167 |
| Example 1-9 | 9 | 4.58 | 5.47 | (0.142, 0.096) | 167 |
| Example 1-10 | 10 | 4.58 | 5.47 | (0.142, 0.096) | 167 |
| Example 1-11 | 11 | 4.51 | 5.48 | (0.142, 0.099) | 147 |
| Example 1-12 | 12 | 4.58 | 5.47 | (0.142, 0.096) | 167 |
| Comparative Example 1-1 | a | 4.88 | 4.12 | (0.152, 0.116) | 95 |
| Comparative Example 1-2 | b | 4.98 | 4.30 | (0.142, 0.096) | 108 |
| Comparative Example 1-3 | c | 4.85 | 4.12 | (0.142, 0.099) | 95 |
| Comparative Example 1-4 | d | 4.87 | 4.30 | (0.142, 0.099) | 108 |
| Comparative Example 1-5 | e | 4.89 | 4.30 | (0.142, 0.099) | 108 |

From the results in Table 1, it can be seen that the heterocyclic compound of Formula 1 can be used for an organic material layer capable of simultaneously performing electron injection and electron transport of the organic light-emitting device.

In addition, comparing Examples 1-1 to 1-12 with Comparative Examples 1-1 to 1-5, it can be confirmed that the compounds of Examples 1-1 to 1-12 having an asymmetrical structure in which the positions 5 and 9 of the central structure of diphenylfuran or diphenylthiophene are substituted as shown in the Formula 1 exhibit superior characteristics in terms of driving voltage, efficiency and lifetime of the organic light-emitting device, as compared with the compounds of Comparative Examples 1-1 to 1-5 having substituents symmetrically arranged on both sides of a central skeleton. This is because the heterocyclic compound of Formula 1 has superior thermal stability and less interaction between the substances, and better characteristics inherent to the material, as compared with a symmetrical type compound.

In addition, comparing Examples 1-7 to 1-12 with Comparative Example 1-1, it can be confirmed that, when an anthracene-based substituent is present in the diphenylthiophene skeleton as in the compound (a) of Comparative Example 1-1, the color purity is significantly decreased, and this is because the anthracene-based light emitting properties also affect the skeleton.

Particularly, in the case of the hetero compounds of Examples 1-1, 1-2, 1-6, 1-7, 1-8 and 1-11, since the HOMO energy is as deep as 6.1 eV or more and electron mobility is high, they exhibit superior characteristics in terms of driving voltage, efficiency, and lifetime when applied to the organic light emitting device.

Further, when the heterocyclic compound of Formula 1 is used for an organic material layer capable of simultaneously performing electron injection and electron transport, the n-type dopant used in the art can be mixed and used. Accordingly, the heterocyclic compound of Formula 1 can have a low driving voltage and a high efficiency, and increase the stability of the device by the hole stability of the compound.

Examples 2-1

A glass substrate on which a thin film of ITO (indium tin oxide) was coated in a thickness of 1,000 Å was put into distilled water containing the detergent dissolved therein and washed by the ultrasonic wave. In this case, the used detergent was a product commercially available from Fischer Co. and the distilled water was one which had been twice filtered by using a filter commercially available from Millipore Co. The ITO was washed for 30 minutes, and ultrasonic washing was then repeated twice for 10 minutes by using distilled water. After the washing with distilled water was completed, the substrate was ultrasonically washed with isopropyl alcohol, acetone, and methanol solvent, and dried, after which it was transported to a plasma cleaner. Then, the substrate was cleaned with oxygen plasma for 5 minutes, and then transferred to a vacuum evaporator.

On the ITO transparent electrode thus prepared, a compound of Formula [HI-A] below was thermally vacuum-deposited in a thickness of 600 Å to form a hole injection layer. Hexanitrile hexaazatriphenylene of Formula [HAT] below (50 Å) and a compound of Formula [HT-A] below (600 Å) were sequentially vacuum-deposited on the hole injection layer to form a hole transport layer.

Then, compounds of Formulas [BH3] and [BH2D] below were vacuum-deposited at a weight ratio of 25:1 on the hole transport layer in a film thickness of 200 Å to form a light emitting layer.

Compound 1 prepared in Preparation Example 1 was vacuum-deposited on the light emitting layer to form an electron control layer with a thickness of 200 Å. The compound of Formula [ET] and Compound of Formula [LiQ] (lithium quinolate) were vacuum-deposited on the electron control layer at a weight ratio of 1:1 to form an electron injection and transport layer with a thickness of 150 Å. Lithium fluoride (LiF) (10 Å) and aluminum (1,000 Å) were sequentially deposited on the electron injection and transport layer to form a cathode.

In the above process, the vapor deposition rate of the organic material was maintained at 0.4 to 0.9 Å/sec, the vapor deposition rate of lithium fluoride of the cathode was maintained at 0.3 Å/sec, the vapor deposition rate of aluminum was maintained at 2 Å/sec, and the degree of vacuum during vapor deposition was maintained at $1 \times 10^{-7}$ to $5 \times 10^{-8}$ torr to manufacture an organic light emitting device.

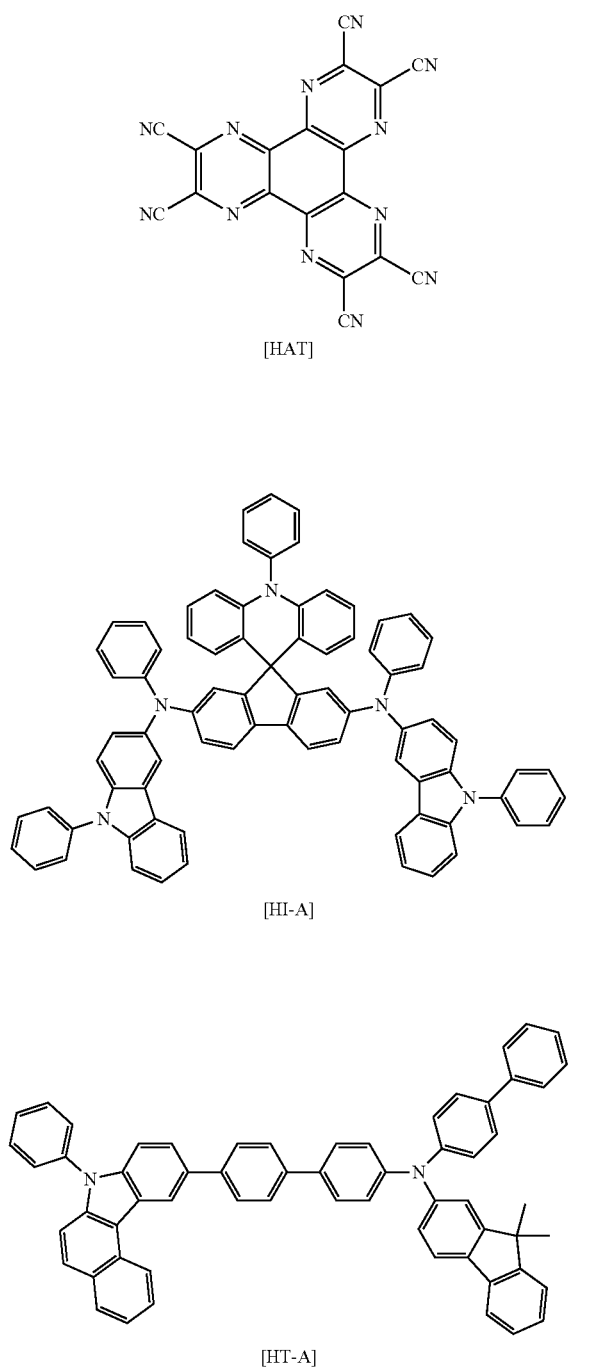

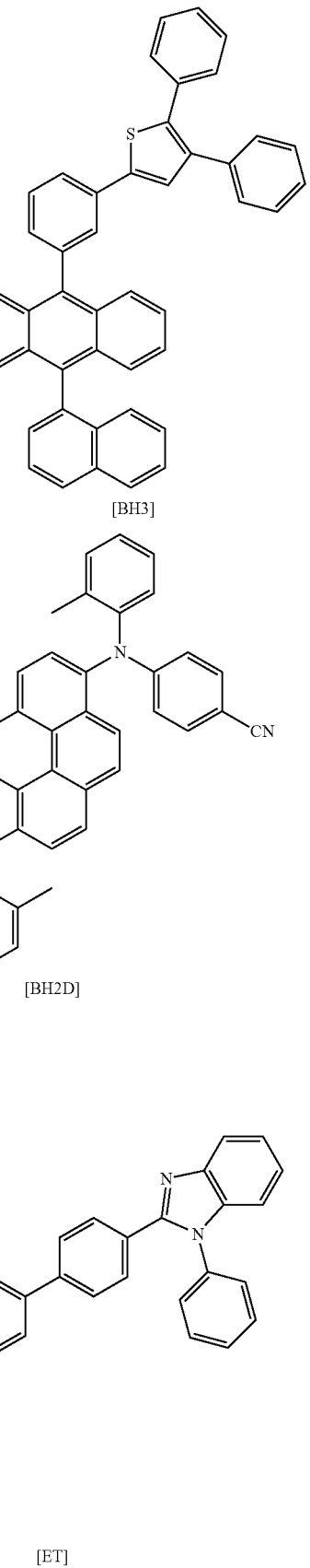

Examples 2-2 to 2-12

The organic light emitting device was manufactured in the same manner as in Example 2-1, except that the compounds shown in Table 2 below were used instead of the compound 1 in Example 2-1.

Comparative Example 2-1 to 2-5

The organic light emitting devices were manufactured in the same manner as in Example 2-1, except that the compounds (a), (b), (c), (d), or (e) having the following structures shown in Table 2 below were used instead of the compound 1 in Example 2-1.

(a)
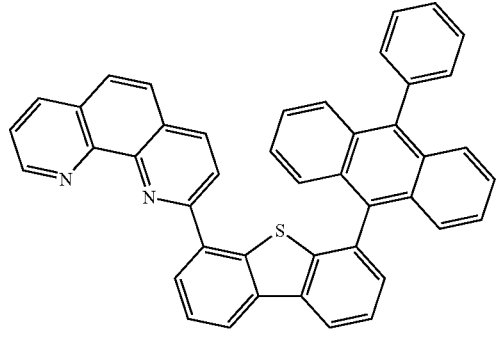

(b)
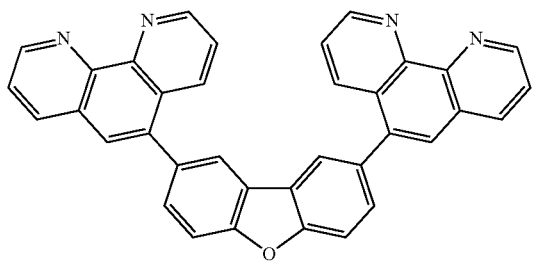

(c)
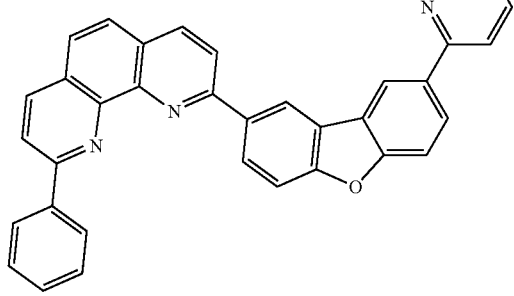

(d)
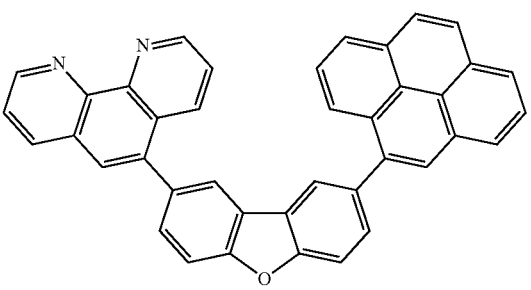

(e)
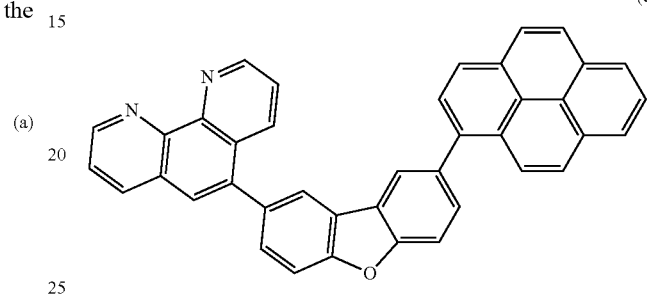

Experimental Example 2

The driving voltage and light emitting efficiency were measured at the current density of 10 mA/cm² for the organic light emitting devices manufactured in the Examples 2-1 to 2-12 and Comparative Examples 2-1 to 2-5, and the time ($T_{90}$) at which the luminance became 90% relative to the initial luminance at the current density of 20 mA/cm² was measured. The results are shown in Table 2 below.

TABLE 2

| | Compound | Voltage (V@10 mA/cm²) | Efficiency (cd/A@10 mA/cm²) | Color coordinate (x, y) | Lifetime (h) $T_{90}$ at 20 mA/cm² |
|---|---|---|---|---|---|
| Example 2-1 | 1 | 4.14 | 5.64 | (0.142, 0.097) | 248 |
| Example 2-2 | 2 | 4.12 | 5.74 | (0.142, 0.097) | 239 |
| Example 2-3 | 3 | 4.20 | 5.62 | (0.142, 0.096) | 280 |
| Example 2-4 | 4 | 4.24 | 5.10 | (0.142, 0.096) | 171 |
| Example 2-5 | 5 | 4.18 | 5.54 | (0.142, 0.096) | 250 |
| Example 2-6 | 6 | 4.23 | 5.50 | (0.142, 0.096) | 263 |
| Example 2-7 | 7 | 4.39 | 5.07 | (0.142, 0.096) | 161 |
| Example 2-8 | 8 | 4.11 | 5.73 | (0.142, 0.099) | 227 |
| Example 2-9 | 9 | 4.26 | 5.00 | (0.142, 0.096) | 160 |
| Example 2-10 | 10 | 4.21 | 5.55 | (0.142, 0.098) | 236 |
| Example 2-11 | 11 | 4.23 | 5.52 | (0.142, 0.096) | 234 |
| Example 2-12 | 12 | 4.11 | 5.57 | (0.142, 0.096) | 270 |
| Comparative Example 2-1 | a | 4.78 | 3.92 | (0.151, 0.109) | 86 |
| Comparative Example 2-2 | b | 4.98 | 4.55 | (0.142, 0.098) | 89 |
| Comparative Example 2-3 | c | 4.79 | 4.55 | (0.142, 0.098) | 171 |

TABLE 2-continued

| Com-pound | Voltage (V@10 mA/cm²) | Efficiency (cd/A@10 mA/cm²) | Color coordinate (x, y) | Lifetime (h) T₉₀ at 20 mA/cm² |
|---|---|---|---|---|
| Comparative Example 2-4 | d | 4.98 | 4.52 | (0.142, 0.096) | 162 |
| Comparative Example 2-5 | e | 4.88 | 4.57 | (0.142, 0.096) | 166 |

From the results in Table 2, it can be seen that the heterocyclic compound of Formula 1 can be used for an electron control layer of the organic light emitting device.

In addition, comparing Examples 2-1 to 2-12 with Comparative Examples 2-1 to 2-5, it can be confirmed that the compounds having asymmetrical structures in which the positions 5 and 9 of the central structure of diphenylfuran or diphenylthiophene are substituted as shown in the Formula 1 are excellent in thermal stability and have deep HOMO levels of 6.0 eV or more, high triplet energies (ET) and hole stability, and therefore, exhibit superior characteristics in terms of driving voltage, efficiency and lifetime of the organic light-emitting device, as compared with the compounds of Comparative Examples 2-1 to 2-5 having substituents symmetrically arranged with regard to a central skeleton of diphenylfuran or diphenylthiophene.

Further, comparing Examples 2-1 to 2-12 with Comparative Example 2-1, it can be confirmed that the compounds of Examples 2-1 to 2-12 exhibit higher color purity than the compound (a) of Comparative Example 2-1 having anthracene as a substituent.

DESCRIPTION OF SYMBOLS

| | |
|---|---|
| 1: substrate, | 2: anode, |
| 3: light emitting layer | 4: cathode |
| 5: hole injection layer | |
| 6: hole transport layer | |
| 7: light emitting layer | |
| 8: electron transport layer | |

The invention claimed is:

1. A compound of Formula 1:

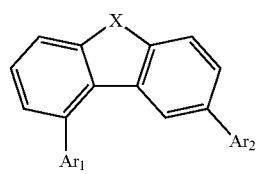

[Formula 1]

wherein in Formula 1:
X is O or S;
Ar₁ is:

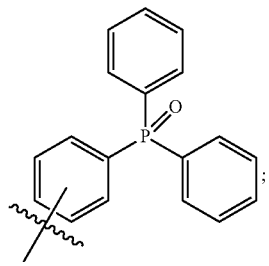

Ar₂ is a functional group of Formula 2 below:

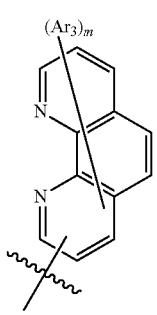

[Formula 2]

wherein in Formula 2:
Ar₃ is phenyl; and
m is an integer of 0 or 1.

2. The compound of claim 1, wherein Ar₁ is

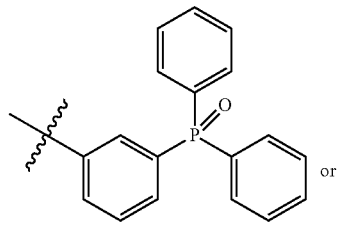

or

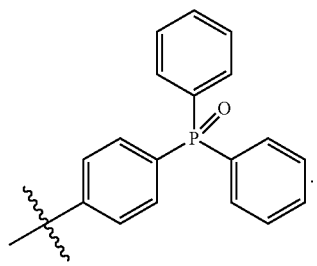

.

3. The compound of claim 1, wherein Ar$_2$ is any one functional group selected from the group consisting of the following functional groups:
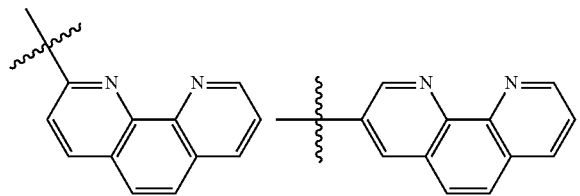
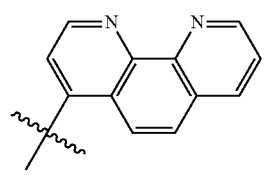
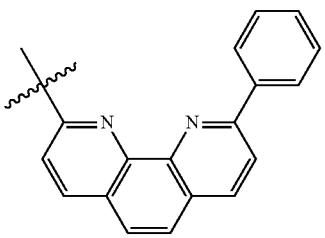
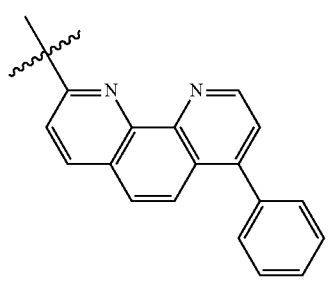
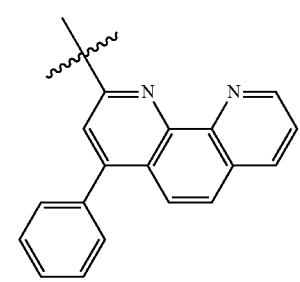
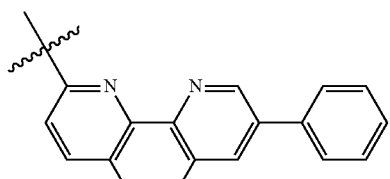
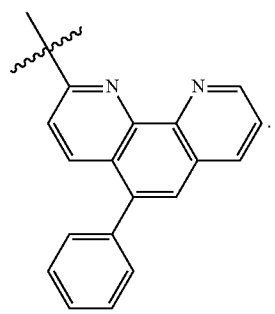
4. The compound of claim 1, wherein the compound is a compound of Formula 1a:
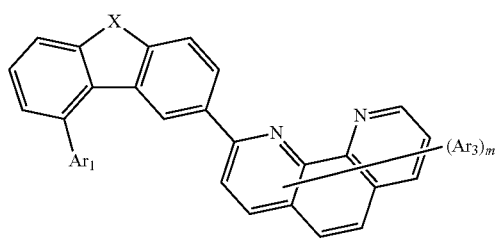
[Formula 1a]
wherein in Formula 1a:
X is O or S;
Ar$_1$ is:
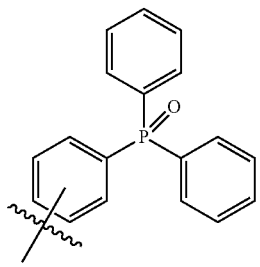
Ar$_3$ is phenyl; and
m is an integer of 0 or 1.

5. The compound of claim 1, wherein the compound is any one compound selected from the group consisting of the following compounds:
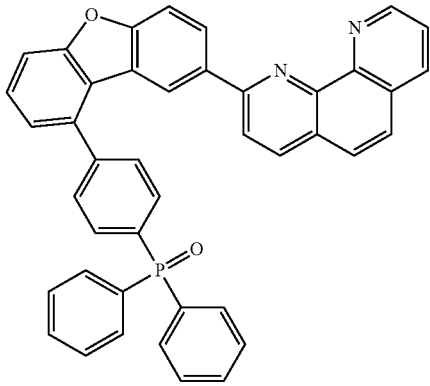
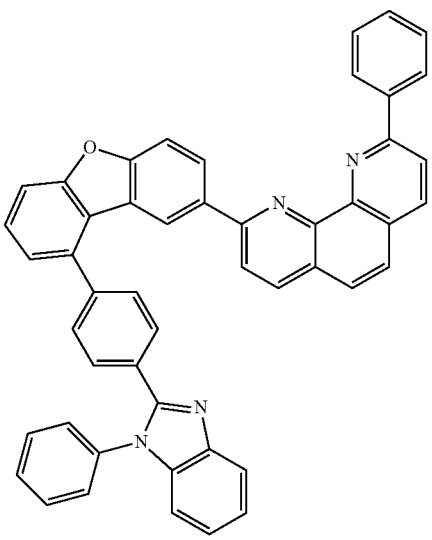
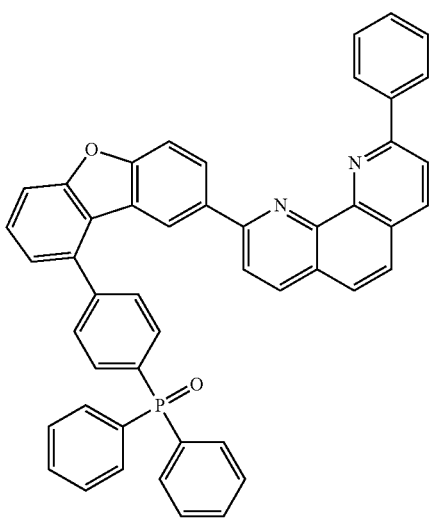
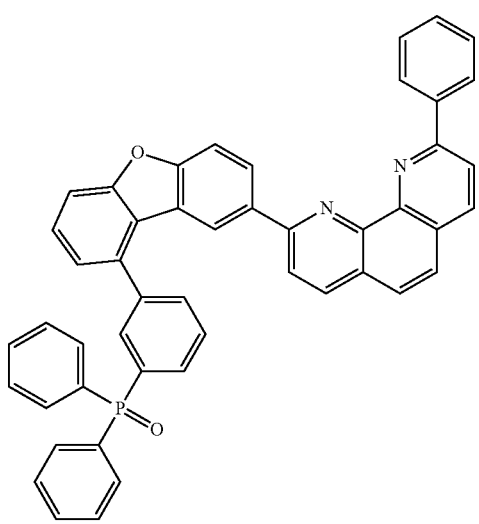
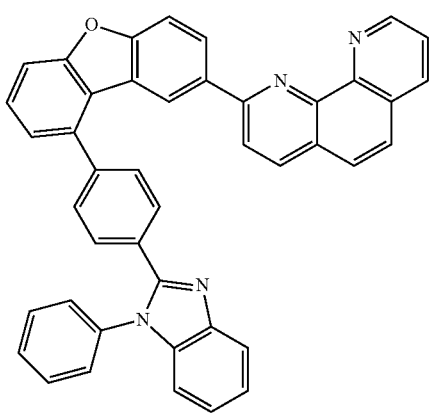 [SMILES: c1ccc(-n2c(-c3ccc(-c4cccc5oc6ccc(-c7ccc8ccc9cccnc9c8n7)cc6c45)cc3)nc3ccccc32)cc1]
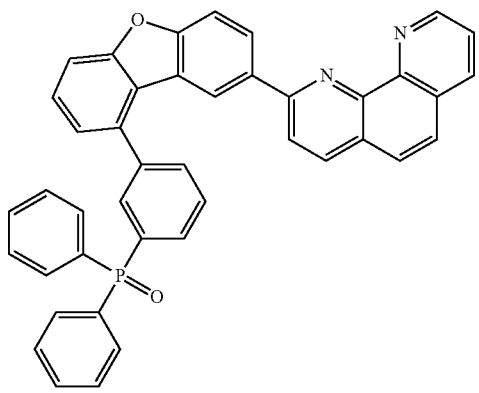

-continued
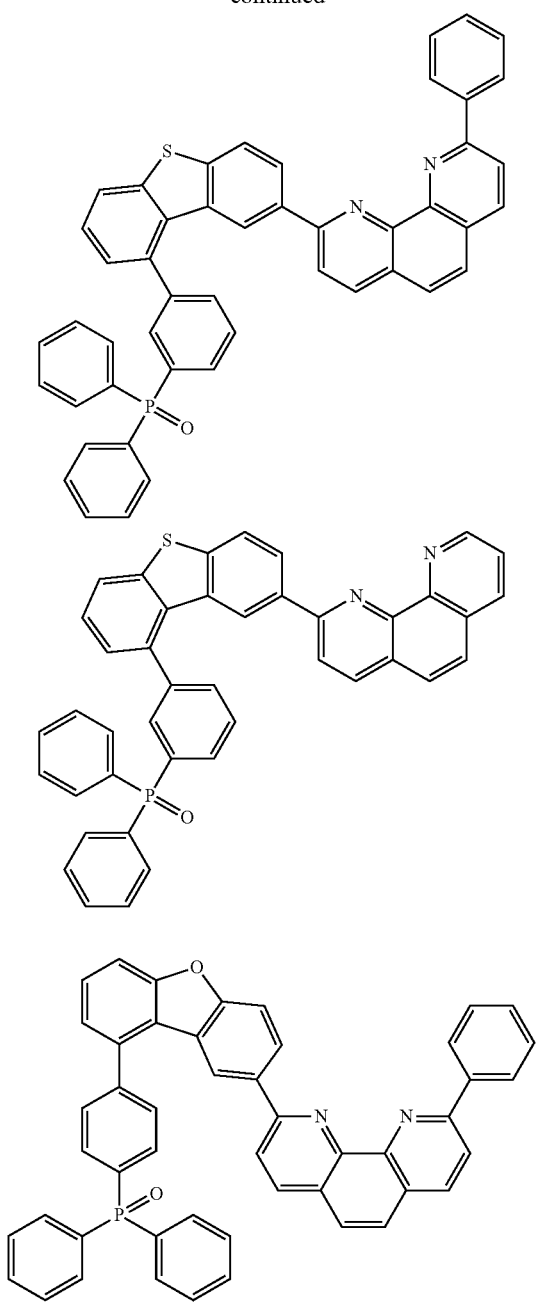
-continued
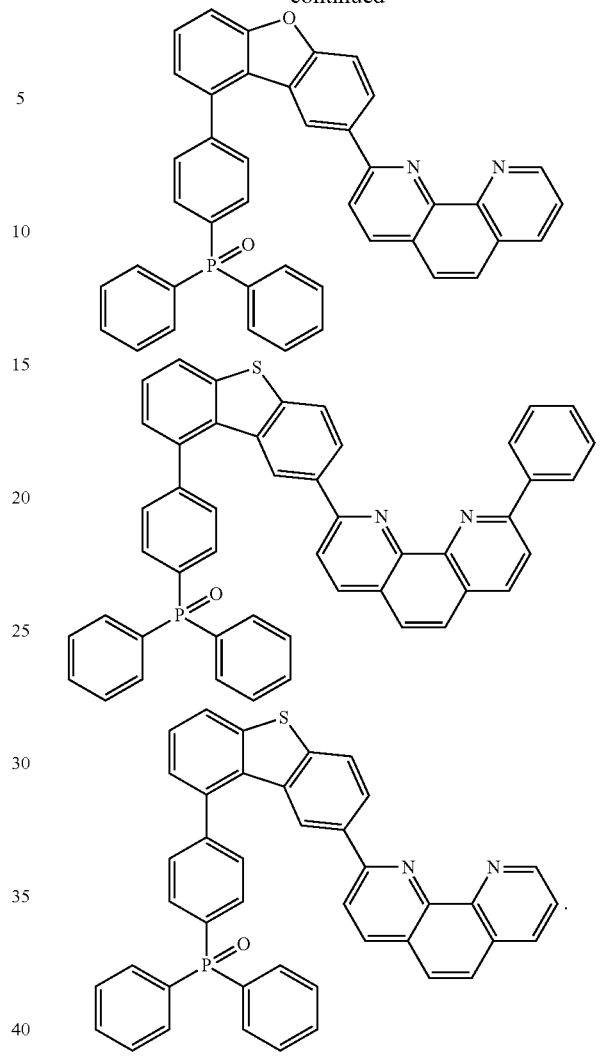
6. An organic light emitting device, comprising:
a first electrode;
a second electrode provided at a side opposite to the first electrode; and
at least one layer of an organic material layer provided between the first electrode and the second electrode, wherein the at least one layer of the organic material layer includes a compound of claim 1.
* * * * *

UNITED STATES PATENT AND TRADEMARK OFFICE
CERTIFICATE OF CORRECTION

| | | |
|---|---|---|
| PATENT NO. | : 11,700,768 B2 | Page 1 of 1 |
| APPLICATION NO. | : 16/475239 | |
| DATED | : July 11, 2023 | |
| INVENTOR(S) | : Jung Hoon Yang et al. | |

It is certified that error appears in the above-identified patent and that said Letters Patent is hereby corrected as shown below:

In the Claims

In Claim 5, the compound shown at Column 73, Lines 50-65 should be deleted.

In Claim 5, the compound shown at Column 74, Lines 3-23 should be deleted.

Signed and Sealed this
Thirtieth Day of January, 2024

Katherine Kelly Vidal
*Director of the United States Patent and Trademark Office*